US006221609B1

(12) United States Patent
Belagaje et al.

(10) Patent No.: US 6,221,609 B1
(45) Date of Patent: *Apr. 24, 2001

(54) ISOLATE NUCLEIC ACID ENCODING HUMAN MGLUR8

(75) Inventors: Rama M. Belagaje; Su Wu, both of Indianapolis, IN (US)

(73) Assignee: Eli Lilly and Company, Indianapolis, IN (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/855,146

(22) Filed: May 13, 1997

Related U.S. Application Data

(60) Provisional application No. 60/021,243, filed on Jul. 3, 1996.
(51) Int. Cl.[7] ............................ C07K 14/705; C12N 15/12
(52) U.S. Cl. ............................ 435/7.1; 435/7.2; 435/69.1; 435/252.3; 435/320.1; 536/23.5
(58) Field of Search ........................ 435/67.1, 7.1, 435/7.2, 252.3, 320.1; 536/23.5

(56) References Cited

U.S. PATENT DOCUMENTS 6,051,688  4/2000  Stormann et al. .................. 530/350

OTHER PUBLICATIONS

Nakanishi, Science, 258:597–603, Oct. 23, 1997.*
Duvoisin et al. The Journal of Neuroscience 15(4):3075–3083, Apr. 1995.*
Flor et al. Neuropharmacology 34(2):149–155, Feb. 1995.*
Amara. Nature 360:420–421, Dec. 3, 1992.*

* cited by examiner

*Primary Examiner*—John Ulm
(74) *Attorney, Agent, or Firm*—Alexander Wilson; Thomas D. Webster

(57) ABSTRACT

This invention describes a novel human glutamate receptor, designated mGluR8. This invention also encompasses nucleic acids encoding this receptor, or a fragment thereof, as well as methods employing this receptor and the nucleic acid compounds.

18 Claims, No Drawings

ISOLATE NUCLEIC ACID ENCODING HUMAN MGLUR8

This application claims the benefit to Provisional application Ser. No. 60/021,243, filed Jul. 3, 1996.

BACKGROUND OF THE INVENTION

In the mammalian central nervous system (CNS), the transmission of nerve impulses is controlled by the interaction between a neurotransmitter, that is released by a sending neuron, and a surface receptor on a receiving neuron, which causes excitation of this receiving neuron. L-Glutamate, which is the most abundant neurotransmitter in the CNS, mediates the major excitatory pathway in mammals, and is referred to as an excitatory amino acid (EAA). The receptors that respond to glutamate are called excitatory amino acid receptors (EAA receptors). See Watkins & Evans, *Annual Reviews in Pharmacology and Toxicology*, 21:165 (1981); Monaghan, Bridges, and Cotman, *Annual Reviews in Pharmacology and Toxicology*, 29:365 (1989); Watkins, Krogsgaard-Larsen, and Honore, *Transactions in Pharmaceutical Science*, 11:25 (1990). The excitatory amino acids are of great physiological importance, playing a role in a variety of physiological processes, such as long-term potentiation (learning and memory), the development of synaptic plasticity, motor control, respiration, cardiovascular regulation, and sensory perception.

Excitatory amino acid receptors are classified into two general types. Receptors that are directly coupled to the opening of cation channels in the cell membrane of the neurons are termed "ionotropic." This type of receptor has been subdivided into at least three subtypes, which are defined by the depolarizing actions of the selective agonists N-methyl-D-aspartate (NMDA), a-amino-3-hydroxy-5-methylisoxazole-4-propionic acid (AMPA), and kainic acid (KA).

The second general type of receptor is the G-protein or second messenger-linked "metabotropic" excitatory amino acid receptor. This second type is coupled to multiple second messenger systems that lead to enhanced phosphoinositide hydrolysis, activation of phospholipase D, increases or decreases in cAMP formation, or changes in ion channel function. Schoepp and Conn, *Trends in Pharmacological Science*, 14:13 (1993). Both types of receptors appear not only to mediate normal synaptic transmission along excitatory pathways, but also participate in the modification of synaptic connections during development and throughout life. Schoepp, Bockaert, and Sladeczek, *Trends in Pharmacological Science*, 11:508 (1990); McDonald and Johnson, *Brain Research Reviews*, 15:41 (1990).

The excessive or inappropriate stimulation of excitatory amino acid receptors leads to neuronal cell damage or loss by way of a mechanism known as excitotoxicity. This process has been suggested to mediate neuronal degeneration in a variety of conditions. The medical consequences of such neuronal degeneration makes the abatement of these degenerative neurological processes an important therapeutic goal.

The metabotropic glutamate receptors are a highly heterogeneous family of glutamate receptors that are linked to multiple second-messenger pathways. These receptors function to modulate the presynaptic release of glutamate, and the postsynaptic sensitivity of the neuronal cell to glutamate excitation. Agonists and antagonists of these receptors may be useful for the treatment of acute and chronic neurodegenerative conditions, and as antipsychotic, anticonvulsant, analgesic, anxiolytic, antidepressant, and anti-emetic agents.

The present invention provides an additional human excitatory amino acid receptor, designated mGluR8, to those previously known. The characterization and treatment of physiological disorders is hereby furthered.

SUMMARY OF THE INVENTION

This invention provides an isolated amino acid compound useful as a human metabotropic glutamate receptor, the compound having the amino acid sequence which is designated as SEQ ID NO:2.

The present invention also provides an isolated nucleic acid compound that comprises a nucleic acid sequence which encodes for the amino acid compounds provided. Particularly this invention provides the isolated nucleic acid compound having the sequence designated as SEQ ID NO:1.

This invention also provides recombinant nucleic acid vectors comprising nucleic acids encoding SEQ ID NO:2. This invention also encompasses recombinant DNA vectors which comprise the isolated DNA sequence which is SEQ ID NO:1.

The present invention also provides assays for determining the efficacy and reaction profile of agents useful in the treatment or prevention of disorders associated with an excess or deficiency in the amount of glutamate present.

DEFINITIONS

The terms and abbreviations used in this document have their normal meanings unless otherwise designated. For example "_C" refers to degrees Celsius; "N" refers to normal or normality; "mM" refers to millimole or millimoles; "g" refers to gram or grams; "ml" means milliliter or milliliters; "M" refers to molar or molarity; "$\mu$g" refers to microgram or micrograms; and "$\mu l$" refers to microliter or microliters.

All nucleic acid sequences, unless otherwise designated, are written in the direction from the 5' end to the 3' end, frequently referred to as "5' to 3'".

All amino acid or protein sequences, unless otherwise designated, are written commencing with the amino terminus ("N-terminus") and concluding with the carboxy terminus ("C-terminus").

"Base pair" or "bp" as used herein refers to DNA or RNA. The abbreviations A,C,G, and T correspond to the 5'-monophosphate forms of the deoxyribonucleosides (deoxy)adenosine, (deoxy)cytidine, (deoxy)guanosine, and (deoxy)thymidine, respectively, when they occur in DNA molecules. The abbreviations U,C,G, and A correspond to the 5'-monophosphate forms of the ribonucleosides urodine, cytidine, guanosine, and adenosine, respectively when they occur in RNA molecules. In double stranded DNA, base pair may refer to a pairing of A with T or C with G. In a DNA/RNA, heteroduplex base pair may refer to a pairing of A with U or C with G. (See the definition of "complementary", infra.)

The terms "cleavage" or "restriction" of DNA refers to the catalytic cleavage of the DNA with a restriction enzyme that acts only at certain sequences in the DNA ("sequence-specific endonucleases"). The various restriction enzymes used herein are commercially available and their reaction conditions, cofactors, and other requirements were used as would be known to one of ordinary skill in the art. Appropriate buffers and substrate amounts for particular restriction enzymes are specified by the manufacturer or can be readily found in the literature.

"Ligation" refers to the process of forming phosphodiester bonds between two nucleic acid fragments (T.

Maniatis, et al., supra., p. 146). Unless otherwise provided, ligation may be accomplished using known buffers and conditions with a DNA ligase, such as T4 DNA ligase.

The term "plasmid" refers to an extrachromosomal (usually) self-replicating genetic element. Plasmids are generally designated by a lower case "p" followed by letters and/or numbers. The starting plasmids herein are either commercially available, publicly available on an unrestricted basis, or can be constructed from available plasmids in accordance with published procedures. In addition, equivalent plasmids to those described are known in the art and will be apparent to the ordinarily skilled artisan.

The term "reading frame" means the nucleotide sequence from which translation occurs "read" in triplets by the translational apparatus of transfer RNA (tRNA) and ribosomes and associated factors, each triplet corresponding to a particular amino acid. A frameshift mutation occurs when a base pair is inserted or deleted from a DNA segment. When this occurs, the result is a different protein from that coded for by the DNA segment prior to the frameshift mutation. To insure against this, the triplet codons corresponding to the desired polypeptide must be aligned in multiples of three from the initiation codon, i.e. the correct "reading frame" being maintained.

"Recombinant DNA cloning vector" as used herein refers to any autonomously replicating agent, including, but not limited to, plasmids and phages, comprising a DNA molecule to which one or more additional DNA segments can or have been added.

The term "recombinant DNA expression vector" as used herein refers to any recombinant DNA cloning vector in which a promoter and other regulatory elements to control transcription of the inserted DNA.

The term "expression vector system" as used herein refers to a recombinant DNA expression vector in combination with one or more trans-acting factors that specifically influence transcription, stability, or replication of the recombinant DNA expression vector. The trans-acting factor may be expressed from a co-transfected plasmid, virus, or other extrachromosomal element, or may be expressed from a gene integrated within the chromosome.

"Transcription" as used herein refers to the process whereby information contained in a nucleotide sequence of DNA is transferred to a complementary RNA sequence.

The term "transfection" as used herein refers to the taking up of an expression vector by a host cell whether or not any coding sequences are in fact expressed. Numerous methods of transfection are known to the ordinarily skilled artisan, for example, calcium phosphate co-precipitation, and electroporation. Successful transfection is generally recognized when any indication of the operation of this vector occurs within the host cell.

The term "transformation" as used herein means the introduction of DNA into an organism so that the DNA is replicable, either as an extrachromosomal element or by chromosomal integration. Methods of transforming bacterial and eukaryotic hosts are well known in the art, many of which methods are summarized in J. Sambrook, et al., "Molecular Cloning: A Laboratory Manual" (1989).

The term "translation" as used herein refers to the process whereby the genetic information of messenger RNA is used to specify and direct the synthesis of a polypeptide chain.

The term "vector" as used herein refers to a nucleic acid compound used for the transformation of cells with polynucleotide sequences corresponding to appropriate protein molecules which when combined with appropriate control sequences confer specific properties on the host cell to be transformed. Plasmids, viruses, and bacteriophage are suitable vectors. Artificial vectors are constructed by joining DNA molecules from different sources. The term "vector" as used herein includes Recombinant DNA cloning vectors and Recombinant DNA expression vectors.

The terms "complementary" or "complementarity" as used herein refers to the pairing of bases, purines and pyrimidines, that associate through hydrogen bonding in double stranded nucleic acid. The following base pairs are complementary: guanine and cytosine; adenine and thymine; and adenine and uracil.

The term "hybridization" as used herein refers to a process in which a strand of nucleic acid joins with a complementary strand through base pairing. The conditions employed in the hybridization of two non-identical, but very similar, complementary nucleic acids varies with the degree of complementarity of the two strands and the length of the strands. Such techniques and conditions are well known to practitioners in this field.

"Isolated amino acid sequence" refers to any amino acid sequence, however constructed or synthesized, which is locationally distinct from the naturally occurring sequence.

"Isolated DNA compound" refers to any DNA sequence, however constructed or synthesized, which is locationally distinct from its natural location in genomic DNA.

"Isolated nucleic acid compound" refers to any RNA or DNA sequence, however constructed or synthesized, which is locationally distinct from its natural location.

A "primer" is a nucleic acid fragment which functions as an initiating substrate for enzymatic or synthetic elongation.

The term "promoter" refers to a DNA sequence which directs transcription of DNA to RNA.

A "probe" as used herein is a nucleic acid compound or a fragment thereof which hybridizes with a nucleic acid compound which encodes either the entire sequence SEQ ID NO:2, a sequence complementary to SEQ ID NO:2, or a part thereof.

The term "stringency" refers to a set of hybridization conditions which may be varied in order to vary the degree of nucleic acid hybridization with another nucleic acid. (See the definition of "hybridization", supra.)

The term "antigenically distinct" as used herein refers to a situation in which antibodies raised against an epitope of the proteins of the present invention, or a fragment thereof, may be used to differentiate between the proteins of the present invention and other glutamate receptor subtypes. This term may also be employed in the sense that such antibodies may be used to differentiate between the human mGluR8 receptor protein and analogous proteins derived from other species.

The term "PCR" as used herein refers to the widely-known polymerase chain reaction employing a thermally-stable polymerase.

DETAILED DESCRIPTION OF THE INVENTION

The present invention provides an isolated amino acid compound useful as a human metabotropic glutamate receptor. The compound comprises the amino acid sequence:

```
Met Val Cys Glu Gly Lys Arg Ser Ala Ser Cys Pro Cys Phe Phe Leu
  1               5                  10                  15

Leu Thr Ala Lys Phe Tyr Trp Ile Leu Thr Met Met Gln Arg Thr His
            20                  25                  30

Ser Gln Glu Tyr Ala His Ser Ile Arg Val Asp Gly Asp Ile Ile Leu
            35                  40                  45

Gly Gly Leu Phe Pro Val His Ala Lys Gly Glu Arg Gly Val Pro Cys
            50                  55                  60

Gly Glu Leu Lys Lys Glu Lys Gly Ile His Arg Leu Glu Ala Met Leu
 65                  70                  75                  80

Tyr Ala Ile Asp Gln Ile Asn Lys Asp Pro Asp Leu Leu Ser Asn Ile
                85                  90                  95

Thr Leu Gly Val Arg Ile Leu Asp Thr Cys Ser Arg Asp Thr Tyr Ala
            100                 105                 110

Leu Glu Gln Ser Leu Thr Phe Val Gln Ala Leu Ile Glu Lys Asp Ala
            115                 120                 125

Ser Asp Val Lys Cys Ala Asn Gly Asp Pro Pro Ile Phe Thr Lys Pro
            130                 135                 140

Asp Lys Ile Ser Gly Val Ile Gly Ala Ala Ala Ser Ser Val Ser Ile
145                 150                 155                 160

Met Val Ala Asn Ile Leu Arg Leu Phe Lys Ile Pro Gln Ile Ser Tyr
                165                 170                 175

Ala Ser Thr Ala Pro Glu Leu Ser Asp Asn Thr Arg Tyr Asp Phe Phe
            180                 185                 190

Ser Arg Val Val Pro Pro Asp Ser Tyr Gln Ala Gln Ala Met Val Asp
            195                 200                 205

Ile Val Thr Ala Leu Gly Trp Asn Tyr Val Ser Thr Leu Ala Ser Glu
            210                 215                 220

Gly Asn Tyr Gly Glu Ser Gly Val Glu Ala Phe Thr Gln Ile Ser Arg
225                 230                 235                 240

Glu Ile Gly Gly Val Cys Ile Ala Gln Ser Gln Lys Ile Pro Arg Glu
                245                 250                 255

Pro Arg Pro Gly Glu Phe Glu Lys Ile Ile Lys Arg Leu Leu Glu Thr
            260                 265                 270

Pro Asn Ala Arg Ala Val Ile Met Phe Ala Asn Glu Asp Asp Ile Arg
            275                 280                 285

Arg Ile Leu Glu Ala Ala Lys Lys Leu Asn Gln Ser Gly His Phe Leu
            290                 295                 300

Trp Ile Gly Ser Asp Ser Trp Gly Ser Lys Ile Ala Pro Val Tyr Gln
305                 310                 315                 320

Gln Glu Glu Ile Ala Glu Gly Ala Val Thr Ile Leu Pro Lys Arg Ala
                325                 330                 335

Ser Ile Asp Gly Phe Asp Arg Tyr Phe Arg Ser Arg Thr Leu Ala Asn
            340                 345                 350

Asn Arg Arg Asn Val Trp Phe Ala Glu Phe Trp Glu Glu Asn Phe Gly
            355                 360                 365

Cys Lys Leu Gly Ser His Gly Lys Arg Asn Ser His Ile Lys Lys Cys
            370                 375                 380

Thr Gly Leu Glu Arg Ile Ala Arg Asp Ser Ser Tyr Glu Gln Glu Gly
385                 390                 395                 400

Lys Val Gln Phe Val Ile Asp Ala Val Tyr Ser Met Ala Tyr Ala Leu
                405                 410                 415

His Asn Met His Lys Asp Leu Cys Pro Gly Tyr Ile Gly Leu Cys Pro
```

-continued

```
                420                425                430
Arg Met Ser Thr Ile Asp Gly Lys Glu Leu Leu Gly Tyr Ile Arg Ala
        435                440                445
Val Asn Phe Asn Gly Ser Ala Gly Thr Pro Val Thr Phe Asn Glu Asn
    450                455                460
Gly Asp Ala Pro Gly Arg Tyr Asp Ile Phe Gln Tyr Gln Ile Thr Asn
465                470                475                480
Lys Ser Thr Glu Tyr Lys Val Ile Gly His Trp Asn Gln Leu His
                485                490                495
Leu Lys Val Glu Asp Met Gln Trp Ala His Arg Glu His Thr His Pro
            500                505                510
Ala Ser Val Cys Ser Leu Pro Cys Lys Pro Gly Glu Arg Lys Lys Thr
            515                520                525
Val Lys Gly Val Peo Cys Cys Trp His Cys Glu Arg Cys Glu Gly Tyr
    530                535                540
Asn Tyr Gln Val Asp Glu Leu Ser Cys Glu Leu Cys Pro Leu Asp Gln
545                550                555                560
Arg Pro Asn Met Asn Arg Thr Gly Cys Gln Leu Ile Pro Ile Ile Lys
                565                570                575
Leu Glu Trp His Ser Pro Trp Ala Val Val Pro Val Phe Val Ala Ile
            580                585                590
Leu Gly Ile Ile Ala Thr Thr Phe Val Ile Val Thr Phe Val Arg Tyr
        595                600                605
Asn Asp Thr Pro Ile Val Arg Ala Ser Gly Arg Glu Leu Ser Tyr Val
    610                615                620
Leu Leu Thr Gly Ile Phe Leu Cys Tyr Ser Ile Thr Phe Leu Met Ile
625                630                635                640
Ala Ala Pro Asp Thr Ile Ile Cys Ser Phe Arg Arg Val Phe Leu Gly
                645                650                655
Leu Gly Met Cys Phe Ser Tyr Ala Ala Leu Leu Thr Lys Thr Asn Arg
            660                665                670
Ile His Arg Ile Phe Glu Gln Gly Lys Lys Ser Val Thr Ala Pro Lys
        675                680                685
Phe Ile Ser Pro Ala Ser Gln Leu Val Ile Thr Phe Ser Leu Ile Ser
    690                695                700
Val Gln Leu Leu Gly Val Phe Val Trp Phe Val Val Asp Pro Pro His
705                710                715                720
Ile Ile Ile Asp Tyr Gly Glu Gln Arg Thr Leu Asp Pro Glu Lys Ala
                725                730                735
Arg Gly Val Leu Lys Cys Asp Ile Ser Asp Leu Ser Leu Ile Cys Ser
            740                745                750
Leu Gly Tyr Ser Ile Leu Leu Met Val Thr Cys Thr Val Tyr Ala Asn
        755                760                765
Lys Thr Arg Gly Val Pro Glu Thr Phe Asn Glu Ala Lys Pro Ile Gly
    770                775                780
Phe Thr Met Tyr Thr Thr Cys Ile Ile Trp Leu Ala Phe Ile Pro Ile
785                790                795                800
Phe Phe Gly Thr Ala Gln Ser Ala Glu Lys Met Tyr Ile Gln Thr Thr
                805                810                815
Thr Leu Thr Val Ser Met Ser Leu Ser Ala Ser Val Ser Leu Gly Met
            820                825                845
Leu Tyr Met Pro Lys Val Tyr Ile Ile Phe His Pro Glu Gln Asn
        835                840                845
```

```
                          -continued
Val Gln Lys Arg Lys Ser Phe Lys Ala Val Val Thr Ala Ala Thr
    850                 855                 860

Met Gln Ser Lys Leu Ile Gln Lys Gly Asn Asp Arg Pro Asn Gly Glu
865                 870                 875                 880

Val Lys Ser Glu Leu Cys Glu Ser Leu Glu Thr Asn Thr Ser Ser Thr
                885                 890                 895

Lys Thr Thr Tyr Ile Ser Tyr Ser Asn His Ser Ile
            900                 905
``` which is hereinafter designated as SEQ ID NO:2.

The present invention also provides an isolated nucleic acid compound that comprises a nucleic acid sequence which encodes for the amino acid compounds provided. Particularly, this invention provides the isolated nucleic acid compound having the sequence:

```
            TGCTGTGTTG CAAGAATAAA CTTTGGGTCT TGGATTGCAA TACCACCTGT GGAGAAA         57

ATG GTA TGC GAG GGA AAG CGA TCA GCC TCT TGC CCT TGT TTC TTC CTC       105
            Met Val Cys Glu Gly Lys Arg Ser Ala Ser Cys Pro Cys Phe Phe Leu
              1               5                  10                  15

TTG ACC GCC AAG TTC TAC TGG ATC CTC ACA ATG ATG CAA AGA ACT CAC       153
            Leu Thr Ala Lys Phe Tyr Trp Ile Leu Thr Met Met Gln Arg Thr His
                            20                  25                  30

AGC CAG GAG TAT GCC CAT TCC ATA CGG GTG GAT GGG GAC ATT ATT TTG       201
            Ser Gln Glu Tyr Ala His Ser Ile Arg Val Asp Gly Asp Ile Ile Leu
                        35                  40                  45

GGG GGT CTC TTC CCT GTC CAC GCA AAG GGA GAG AGA GGG GTG CCT TGT       249
            Gly Gly Leu Phe Pro Val His Ala Lys Gly Glu Arg Gly Val Pro Cys
                    50                  55                  60

GGG GAG CTG AAG AAG GAA AAG GGG ATT CAC AGA CTG GAG GCC ATG CTT       297
            Gly Glu Leu Lys Lys Glu Lys Gly Ile His Arg Leu Glu Ala Met Leu
                65                  70                  75                  80

TAT GCA ATT GAC CAG ATT AAC AAG GAC CCT GAT CTC CTT TCC AAC ATC       345
            Tyr Ala Ile Asp Gln Ile Asn Lys Asp Pro Asp Leu Leu Ser Asn Ile
                            85                  90                  95

ACT CTG GGT GTC CGC ATC CTC GAC ACG TGC TCT AGG GAC ACC TAT GCT       393
            Thr Leu Gly Val Arg Ile Leu Asp Thr Cys Ser Arg Asp Thr Tyr Ala
                        100                 105                 110

TTG GAG CAG TCT CTA ACA TTC GTG CAG GCA TTA ATA GAG AAA GAT GCT       441
            Leu Glu Gln Ser Leu Thr Phe Val Gln Ala Leu Ile Glu Lys Asp Ala
                    115                 120                 125

TCG GAT GTG AAG TGT GCT AAT GGA GAT CCA CCC ATT TTC ACC AAG CCC       489
            Ser Asp Val Lys Cys Ala Asn Gly Asp Pro Pro Ile Phe Thr Lys Pro
                130                 135                 140

AGC AAG ATT TCT GGC GTC ATA GGT GCT GCA GCA AGC TCC GTG TCC ATC       537
            Asp Lys Ile Ser Gly Val Ile Gly Ala Ala Ala Ser Ser Val Ser Ile
            145                 150                 155                 160

ATG GTT GCT AAC ATT TTA AGA CTT TTT AAG ATA CCT CAA ATC AGC TAT       585
            Met Val Ala Asn Ile Leu Arg Leu Phe Lys Ile Pro Gln Ile Ser Tyr
                            165                 170                 175

GCA TCC ACA GCC CCA GAG CTA AGT GAT AAC ACC AGG TAT GAC TTT TTC       633
            Ala Ser Thr Ala Pro Glu Leu Ser Asp Asn Thr Arg Tyr Asp Phe Phe
                        180                 185                 190

TCT CGA GTG GTT CCG CCT GAC TCC TAC CAA GCC CAA GCC ATG GTG GAC       681
            Ser Arg Val Val Pro Pro Asp Ser Tyr Gln Ala Gln Ala Met Val Asp
                    195                 200                 205

ATC GTG ACA GCA CTG GGA TGG AAT TAT GTT TCG ACA CTG GCT TCT GAG       729
            Ile Val Thr Ala Leu Gly Trp Asn Tyr Val Ser Thr Leu Ala Ser Glu
                210                 215                 220

GGG AAC TAT GGT GAG AGC GGT GTG GAG GCC TTC ACC CAG ATC TCG AGG       777
            Gly Asn Tyr Gly Glu Ser Gly Val Glu Ala Phe Thr Gln Ile Ser Arg
```

-continued

```
               225                 230                 235                 240
GAG ATT GGT GGT GTT TGC ATT GCT CAG TCA CAG AAA ATC CCA CGT GAA         825
Glu Ile Gly Gly Val Cys Ile Ala Gln Ser Gln Lys Ile Pro Arg Glu
                    245                 250                 255

CCA AGA CCT GGA GAA TTT GAA AAA ATT ATC AAA CGC CTG CTA GAA ACA         873
Pro Arg Pro Gly Glu Phe Glu Lys Ile Ile Lys Arg Leu Leu Glu Thr
                260                 265                 270

CCT AAT GCT CGA GCA GTG ATT ATG TTT GCC AAT GAG GAT GAC ATC AGG         921
Pro Asn Ala Arg Ala Val Ile Met Phe Ala Asn Glu Asp Asp Ile Arg
                275                 280                 285

AGG ATA TTG GAA GCA GCA AAA AAA CTA AAC CAA AGT GGG CAT TTT CTC         969
Arg Ile Leu Glu Ala Ala Lys Lys Leu Asn Gln Ser Gly His Phe Leu
    290                 295                 300

TGG ATT GGC TCA GAT AGT TGG GGA TCC AAA ATA GCA CCT GTC TAT CAG        1017
Trp Ile Gly Ser Asp Ser Trp Gly Ser Lys Ile Ala Pro Val Tyr Gln
305                 310                 315                 320

CAA GAG GAG ATT GCA GAA GGG GCT GTG ACA ATT TTG CCC AAA CGA GCA        1065
Gln Glu Glu Ile Ala Glu Gly Ala Val Thr Ile Leu Pro Lys Arg Ala
                325                 330                 335

TCA ATT GAT GGA TTT GAT CGA TAC TTT AGA AGC CGA ACT CTT GCC AAT        1113
Ser Ile Asp Gly Phe Asp Arg Tyr Phe Arg Ser Arg Thr Leu Ala Asn
                340                 345                 350

AAT CGA AGA AAT GTG TGG TTT GCA GAA TTC TGG GAG GAG AAT TTT GGC        1161
Asn Arg Arg Asn Val Trp Phe Ala Glu Phe Trp Glu Glu Asn Phe Gly
            355                 360                 365

TGC AAG TTA GGA TCA CAT GGG AAA AGG AAC AGT CAT ATA AAG AAA TGC        1209
Cys Lys Leu Gly Ser His Gly Lys Arg Asn Ser His Ile Lys Lys Cys
    370                 375                 380

ACA GGG CTG GAG CGA ATT GCT CGG GAT TCA TCT TAT GAA CAG GAA GGA        1257
Thr Gly Leu Glu Arg Ile Ala Arg Asp Ser Ser Tyr Glu Gln Glu Gly
385                 390                 395                 400

AAG GTC CAA TTT GTA ATT GAT GCT GTA TAT TCC ATG GCT TAC GCC CTG        1305
Lys Val Gln Phe Val Ile Asp Ala Val Tyr Ser Met Ala Tyr Ala Leu
                405                 410                 415

CAC AAT ATG CAC AAA GAT CTC TGC CCT GGA TAC ATT GGC CTT TGT CCA        1353
His Asn Met His Lys Asp Leu Cys Pro Gly Tyr Ile Gly Leu Cys Pro
                420                 425                 430

CGA ATG AGT ACC ATT GAT GGG AAA GAG CTA CTT GGT TAT ATT CGG GCT        1401
Arg Met Ser Thr Ile Asp Gly Lys Glu Leu Leu Gly Tyr Ile Arg Ala
            435                 440                 445

GTA AAT TTT AAT GGC AGT GCT GGC ACT CCT GTC ACT TTT ATT GAA AAC        1449
Val Asn Phe Asn Gly Ser Ala Gly Thr Pro Val Thr Phe Asn Glu Asn
    450                 455                 460

GGA GAT GCT CCT GGA CGT TAT GAT ATC TTC CAG TAT CAA ATA ACC AAC        1497
Gly Asp Ala Pro Gly Arg Tyr Asp Ile Phe Gln Tyr Gln Ile Thr Asn
465                 470                 475                 480

AAA AGC ACA GAG TAC AAA GTC ATC GGC CAC TGG ACC AAT CAG CTT CAT        1545
Lys Ser Thr Glu Tyr Lys Val Ile Gly His Trp Thr Asn Gln Leu His
                485                 490                 495

CTA AAA GTG GAA GAC ATG CAG TGG GCT CAT AGA GAA CAT ACT CAC CCG        1593
Leu Lys Val Glu Asp Met Gln Tro Ala His Arg Glu his Thr His Pro
                500                 505                 510

GCG TCT GTC TGC AGC CTG CCG TGT AAG CCA GGG GAG AGG AAG AAA ACG        1641
Ala Ser Val Cys Ser Leu Pro Cys Lys Pro Gly Glu Arg Lys Lys Thr
            515                 520                 525

GTA AAA GGG GTC CCT TGC TGC TGG CAC TGT GAA CGC TGT GAA GGT TAC        1689
Val Lys Gly Val Pro Cys Cys Trp His Cys Glu Arg Cys Glu Gly Tyr
    530                 535                 540

AAC TAC CAG GTG GAT GAG CTG TCC TGT GAA CTT TGC CCT CTG GAT CAG        1737
Asn Tyr Gln Val Asp Glu Leu Ser Cys Glu Leu Cys Pro Leu Asp Gln
```

-continued

| | | | | | | | | | | | | | | | | |
|---|---|---|---|---|---|---|---|---|---|---|---|---|---|---|---|---|
| | 545 | | | | 550 | | | | 555 | | | | 560 | | | |
| AGA | CCC | AAC | ATG | AAC | CGC | ACA | GGC | TGC | CAG | CTT | ATC | CCC | ATC | ATC | AAA | 1785 |
| Arg | Pro | Asn | Met | Asn | Arg | Thr | Gly | Cys | Gln | Leu | Ile | Pro | Ile | Ile | Lys | |
| | | | | 565 | | | | | 570 | | | | | 575 | | |
| TTG | GAG | TGG | CAT | TCT | CCC | TGG | GCT | GTG | GTG | CCT | GTG | TTT | GTT | GCA | ATA | 1833 |
| Leu | Glu | Trp | His | Ser | Pro | Trp | Ala | Val | Val | Pro | Val | Phe | Val | Ala | Ile | |
| | | | 580 | | | | | 585 | | | | | 590 | | | |
| TGG | GGA | ATC | ATC | GCC | ACC | ACC | TTT | GTG | ATC | GTG | ACC | TTT | GTC | CGC | TAT | 1881 |
| Leu | Gly | Ile | Ile | Ala | Thr | Thr | Phe | Val | Ile | Val | Thr | Phe | Val | Arg | Tyr | |
| | | 595 | | | | | 600 | | | | | 605 | | | | |
| AAT | GAC | ACA | CCT | ATC | GTG | AGG | GCT | TCA | GGA | CGC | GAA | CTT | AGT | TAC | GTG | 1929 |
| Asn | Asp | Thr | Pro | Ile | Val | Arg | Ala | Ser | Gly | Arg | Glu | Leu | Ser | Tyr | Val | |
| 610 | | | | | 615 | | | | | 620 | | | | | | |
| CTC | CTA | ACG | GGG | ATT | TTT | CTC | TGT | TAT | TCA | ATC | ACG | TTT | TTA | ATG | ATT | 1977 |
| Leu | Leu | Thr | Gly | Ile | Phe | Leu | Cys | Tyr | Ser | Ile | Thr | Phe | Leu | Met | Ile | |
| 625 | | | | | 630 | | | | | 635 | | | | | 640 | |
| GCA | GCA | CCA | GAT | ACA | ATA | ATA | TGC | TCC | TTC | CGA | CGG | GTC | TTC | CTA | GGA | 2025 |
| Ala | Ala | Pro | Asp | Thr | Ile | Ile | Cys | Ser | Phe | Arg | Arg | Val | Phe | Leu | Gly | |
| | | | | 645 | | | | | 650 | | | | | 655 | | |
| CTT | GGC | ATG | TGT | TTC | AGC | TAT | GCA | GCC | CTT | CTG | ACC | AAA | ACA | AAC | CGT | 2073 |
| Leu | Gly | Met | Cys | Phe | Ser | Tyr | Ala | Ala | Leu | Leu | Thr | Lys | Thr | Asn | Arg | |
| | | | 660 | | | | | 665 | | | | | 670 | | | |
| ATC | CAC | CGA | ATA | TTT | GAG | CAG | GGG | AAG | AAA | TCT | GTC | ACA | GCG | CCC | AAG | 2121 |
| Ile | His | Arg | Ile | Phe | Glu | Gln | Gly | Lys | Lys | Ser | Val | Thr | Ala | Pro | Lys | |
| | | 675 | | | | | 680 | | | | | 685 | | | | |
| TTC | ATT | AGT | CCA | GCA | TCT | CAG | CTG | GTG | ATC | ACC | TTC | AGC | CTC | ATC | TCC | 2169 |
| Phe | Ile | Ser | Pro | Ala | Ser | Gln | Leu | Val | Ile | Thr | Phe | Ser | Leu | Ile | Ser | |
| | | 690 | | | | | 695 | | | | | 700 | | | | |
| GTC | CAG | CTC | CTT | GGA | GTG | TTT | GTC | TGG | TTT | GTT | GTG | GAT | CCC | CCC | CAC | 2217 |
| Val | Gln | Leu | Leu | Gly | Val | Phe | Val | Trp | Phe | Val | Val | Asp | Pro | Pro | His | |
| 705 | | | | | 710 | | | | | 715 | | | | | 720 | |
| ATC | ATC | ATT | GAC | TAT | GGA | GAG | CAG | CGG | ACA | CTA | GAT | CCA | GAG | AAG | GCC | 2265 |
| Ile | Ile | Ile | Asp | Tyr | Gly | Glu | Gln | Arg | Thr | Leu | Asp | Pro | Glu | Lys | Ala | |
| | | | | 725 | | | | | 730 | | | | | 735 | | |
| AGG | GGA | GTG | CTC | AAG | TGT | GAC | ATT | TCT | GAT | CTC | TCA | CTC | ATT | TGT | TCA | 2313 |
| Arg | Gly | Val | Leu | Lys | Cys | Asp | Ile | Ser | Asp | Leu | Ser | Leu | Ile | Cys | Ser | |
| | | | 740 | | | | | 745 | | | | | 750 | | | |
| CTT | GGA | TAC | AGT | ATC | CTC | TTG | ATG | GTC | ACT | TGT | ACT | GTT | TAT | GCC | AAT | 2361 |
| Leu | Gly | Tyr | Ser | Ile | Leu | Leu | Met | Val | Thr | Cys | Thr | Val | Tyr | Ala | Asn | |
| | | | 755 | | | | | 760 | | | | | 765 | | | |
| AAA | ACG | AGA | GGT | GTC | CGA | GAG | ACT | TTC | AAT | GAA | GCC | AAA | CCT | ATT | GGA | 2409 |
| Lys | Thr | Arg | Gly | Val | Pro | Glu | Thr | Phe | Asn | Glu | Ala | Lys | Pro | Ile | Gly | |
| 770 | | | | | 775 | | | | | 780 | | | | | | |
| TTT | ACC | ATG | TAT | ACC | ACC | TGC | ATC | ATT | TGG | TTA | GCT | TTC | ATC | CCC | ATC | 2457 |
| Phe | Thr | Met | Tyr | Thr | Thr | Cys | Ile | Ile | Trp | Leu | Ala | Phe | Ile | Pro | Ile | |
| 785 | | | | | 790 | | | | | 795 | | | | | 800 | |
| TTT | TTT | GGT | ACA | GCC | CAG | TCA | GCA | GAA | AAG | ATG | TAC | ATC | CAG | ACA | ACA | 2505 |
| Phe | Phe | Gly | Thr | Ala | Gln | Ser | Ala | Glu | Lys | Met | Tyr | Ile | Gln | Thr | Thr | |
| | | | | 805 | | | | | 810 | | | | | 815 | | |
| ACA | CTT | ACT | GTC | TCC | ATG | AGT | TTA | AGT | GCT | TCA | GTA | TCT | CTG | GGC | ATG | 2553 |
| Thr | Leu | Thr | Val | Ser | Met | Ser | Leu | Ser | Ala | Ser | Val | Ser | Leu | Gly | Met | |
| | | | | 820 | | | | | 825 | | | | | 830 | | |
| CTC | TAT | ATG | CCC | AAG | GTT | TAT | ATT | ATA | ATT | TTT | CAT | CCA | GAA | CAG | AAT | 2601 |
| Leu | Tyr | Met | Pro | Lys | Val | Tyr | Ile | Ile | Ile | Phe | His | Pro | Glu | Gln | Asn | |
| | | | | 835 | | | | | 840 | | | | | 845 | | |
| GTT | CAA | AAA | CGC | AAG | AGG | AGC | TTC | AAG | GCT | GTG | GTG | ACA | GCT | GCC | ACC | 2649 |
| Val | Gln | Lys | Arg | Lys | Arg | Ser | Phe | Lys | Ala | Val | Val | Thr | Ala | Ala | Thr | |
| | | 850 | | | | | 855 | | | | | 860 | | | | |
| ATG | CAA | AGC | AAA | CTG | ATC | CAA | AAA | GGA | AAT | GAC | AGA | CCA | AAT | GGC | GAG | 2697 |
| Met | Gln | Ser | Lys | Leu | Ile | Gln | Lys | Gly | Asn | Asp | Arg | Pro | Asn | Gly | Glu | |

-continued

```
865                 870                 875                 880

GTG AAA AGT GAA CTC TGT GAG AGT CTT GAA ACC AAC ACT TCC TCT ACC    2745
Val Lys Ser Glu Leu Cys Glu Ser Leu Glu Thr Asn Thr Ser Ser Thr
                        885                 890                 895

AAG ACA ACA TAT ATC AGT TAC AGC AAT CAT TCA ATC TGAAACAGGG         2791
Lys Thr Thr Tyr Ile Ser Tyr Ser Asn His Ser Ile
                900                 905

AAATGGCACA ATCTGAAGAG ACGTGGTATA TGATCTTAAA TGATGAACAT GAGACCGCAA  2851

AAATTCACTC CTGGAGATCT CCGTAGACTA CAATCAATCA AATCAATAGT CAGTCTTGTA  2911

AGGAACAAAA ATTAGCCATG AGCCAAAAGT ATCAATAAAC GGGGAGTGAA GAAACCCGTT  2971

TTATACAATA AAACCAATGA GTGTCAAGCT AAAGTATTGC TTATTCATGA GCAGTTAAAA  3031

CAAATCACAA AAGGAAAACT AATGTTAGCT CGTGAAAAAA ATGCTGTTGA AATAAATAAT  3091

GTCTGATGTT ATTCTTGTAT TTTTCTGTGA TTGTGAGAAC TCCCGTTCCT GTCCCACATT  3151

GTTTAACTTG TATAAGACAA TGAGTCTGTT TCTTGTAATG GCTGACCAGA TTGAAGCCCT  3211

GGGTTGTGCT AAAAATAAAT GCAATGATTG ATGCATGCAA TTTTTTATAC AAATAATTTA  3271

TTTCTAATAA TAAAGGAATG TTTTGCAAAA AAAAAAAAAA AAAACTCGAG             3321
``` which is hereinafter designated as SEQ ID NO:1. Preferably, the nucleic acid compound is a compound encompassing nucleotides 58 through 2781 of SEQ ID NO:1.

The present invention provides the protein of SEQ ID NO:2, a human metabotropic glutamate receptor, designated as a mGluR8 receptor using the nomenclature system described in D. D. Schoepp, "Glutamate receptors", *Handbook of Receptors and Channels,* Chapter 13 (S. J. Peroutka, ed., CRC Press, 1984). This receptor is believed to potentiate central nervous system responses and is, therefore, an important target for pharmaceutical purposes.

Skilled artisans will recognize that the proteins of the present invention can be isolated from retina tissue or synthesized by a number of different methods. All of the amino acid compounds of the invention can be made by chemical methods well known in the art, including solid phase peptide synthesis, or recombinant methods. Both methods are described in U.S. Pat. No. 4,617,149, incorporated herein by reference.

The principles of solid phase chemical synthesis of polypeptides are well known in the art and may be found in general texts in the area. See. e.a., H. Dugas and C. Penney, *Bioorganic Chemistry* (1981) Springer-Verlag, N.Y., pgs. 54–92. For example, peptides may be synthesized by solid-phase methodology utilizing an Applied Biosystems 430A peptide synthesizer (commercially available from Applied Biosystems, Foster City Calif.) and synthesis cycles supplied by Applied Biosystems. Protected amino acids, such as t-butoxycarbonyl-protected amino acids, and other reagents are commercially available from many chemical supply houses.

Sequential t-butoxycarbonyl chemistry using double couple protocols are applied to the starting p-methyl benzhydryl amine resins for the production of C-terminal carboxamides. For the production of C-terminal acids, the corresponding pyridine-2-aldoxime methiodide resin is used. Asparagine, glutamine, and arginine are coupled using preformed hydroxy benzotriazole esters. The following side chain protection may be used:

Arg, Tosyl
Asp, cyclohexyl
Glu, cyclohexyl
Ser, Benzyl
Thr, Benzyl
Tyr, 4-bromo carbobenzoxy Removal of the t-butoxycarbonyl moiety (deprotection) may be accomplished with trifluoroacetic acid (TFA) in methylene chloride. Following completion of the synthesis the peptides may be deprotected and cleaved from the resin with anhydrous hydrogen fluoride containing 10% meta-cresol. Cleavage of the side chain protecting group(s) and of the peptide from the resin is carried out at zero degrees Celsius or below, preferably –20_C. for thirty minutes followed by thirty minutes at 0_C.

After removal of the hydrogen fluoride, the peptide/resin is washed with ether, and the peptide extracted with glacial acetic acid and then lyophilized. Purification is accomplished by size-exclusion chromatography on a Sephadex G-10 (Pharmacia) column in 10% acetic acid.

The proteins of the present invention may also be produced by recombinant methods. Recombinant methods are preferred if a high yield is desired. A general method for the construction of any desired DNA sequence is provided in J. Brown, et al., *Methods in Enzymology,* 68:109 (1979). See also, J. Sambrook, et al., supra.

The basic steps in the recombinant production of desired proteins are:

a) construction of a natural, synthetic or semi-synthetic DNA encoding the protein of interest;

b) integrating said DNA into an expression vector in a manner suitable for the expression of the protein of interest, either alone or as a fusion protein;

c) transforming an appropriate eukaryotic or prokaryotic host cell with said expression vector, d) culturing said transformed or transfected host cell in a manner to express the protein of interest; and e) recovering and purifying the recombinantly produced protein of interest.

In general, prokaryotes may be used for cloning of DNA sequences and constructing the vectors of this invention. Prokaryotes may also be employed in the production of the protein of interest. For example, the *Escherichia coli* K12 strain 294 (ATCC No. 31446) is particularly useful for the prokaryotic expression of foreign proteins. Other strains of E. coli which may be used (and their relevant genotypes) include the following strains in Table I:

TABLE I

| Strain | Genotype |
|---|---|
| DH5α | F⁻ (φ80dlacZΔM15), Δ(lacZYA-argF)U169 supE44, λ⁻, hsdR17($r_K^-$, $m_K^+$), recA1, endA1, gyrA96, thi-1, relA1 |
| HB101 | supE44, hsdS20($r_B^-$ $m_B^-$), recA13, ara-14, proA2 lacY1, galK2, rpsL20, xyl-5, mtl-1, mcrB, mrr |
| JM109 | recA1, e14⁻(mcrA), supE44, endA1, hsdR17($r_K^-$, $m_K^+$), gyrA96, relA1, thi-1, Æ(lac-proAB), F'[traD36, proAB+ lacI$^q$, lacZÆM15] |
| RR1 | supE44, hsdS20($r_B^-$ $m_B^-$), ara-14 proA2, lacY1, galK2, rpsL20, xyl-5, mtl-5 |
| χ1776 | F⁻, ton, A53, dapD8, minA1, supE42 (glnV42), Δ(gal-uvrB)40, minB2, rfb-2, gyrA25, thyA142, oms-2, metC65, oms-1, Δ(bioH-asd)29, cycB2, cycA1, hsdR2, λ⁻ |
| 294 | endA, thi⁻, hsr⁻, hsm$_k^+$ (U.S. Pat. 4,366,246) |
| XL1 Blue | recA1, endA1, gyrA96, thi, hsdR17($r_k$, $m_k$+), supE44, relA1, λ-, Æ(lac), [F', proAB, laclqZÆM15, Tn10(tet$^R$)] |

These strains are all commercially available from suppliers such as: Bethesda Research Laboratories, Gaithersburg, Md. 20877 and Stratagene Cloning Systems, La Jolla, Calif. 92037; or are readily available to the public from sources such as the American Type Culture Collection, 12301 Parklawn Drive, Rockville, Md., 10852-1776.

Except where otherwise noted, these bacterial strains can be used interchangeably. The genotypes listed are illustrative of many of the desired characteristics for choosing a bacterial host and are not meant to limit the invention in any way or manner. The genotype designations are in accordance with standard nomenclature. See, for example, J. Sambrook, et al., supra.

In addition to the strains of E. coli discussed supra, bacilli such as Bacillus subtilis, other enterobacteriaceae such as Salmonella typhimurium or Serratia marcescans, and various Pseudomonas species may be used. In addition to these gram-negative bacteria, other bacteria, especially Streptomyces, spp., may be employed in the prokaryotic cloning and expression of the proteins of this invention.

Promoters suitable for use with prokaryotic hosts include the β-lactamase [vector pGX2907 (ATCC 39344) contains the replicon and β-lactamase gene] and lactose promoter systems [Chang et al., Nature (London), 275:615 (1978); and Goeddel et al., Nature (London), 281:544 (1979)], alkaline phosphatase, the tryptophan (trp) promoter system [vector pATH1 (ATCC 37695) is designed to facilitate expression of an open reading frame as a trpE fusion protein under control of the trp promoter] and hybrid promoters such as the tac promoter (isolatable from plasmid pDR540 ATCC-37282). However, other functional bacterial promoters, whose nucleotide sequences are generally known, enable one of skill in the art to ligate them to DNA encoding the proteins of the instant invention using linkers or adapters to supply any required restriction sites. Promoters for use in bacterial systems also will contain a Shine-Dalgarno sequence operably linked to the DNA encoding the desired polypeptides. These examples are illustrative rather than limiting.

The proteins of this invention may be synthesized either by direct expression or as a fusion protein comprising the protein of interest as a translational fusion with another protein or peptide which may be removable by enzymatic or chemical cleavage. It is often observed in the production of certain peptides in recombinant systems that expression as a fusion protein prolongs the lifespan, increases the yield of the desired peptide, or provides a convenient means of purifying the protein of interest. A variety of peptidases (e.g. enterokinase and thrombin) which cleave a polypeptide at specific sites or digest the peptides from the amino or carboxy termini (e.g. diaminopeptidase) of the peptide chain are known. Furthermore, particular chemicals (e.g. cyanogen bromide) will cleave a polypeptide chain at specific sites. The skilled artisan will appreciate the modifications necessary to the amino acid sequence (and synthetic or semi-synthetic coding sequence if recombinant means are employed) to incorporate site-specific internal cleavage sites. See e.g., P. Carter, "Site Specific Proteolysis of Fusion Proteins", Chapter 13 in *Protein Purification: From Molecular Mechanisms to Large Scale Processes,* American Chemical Society, Washington, D.C. (1990).

In addition to cloning and expressing the genes of interest in the prokaryotic systems as discussed above, the proteins of the present invention may also be produced in eukaryotic systems. The present invention is not limited to use in any particular eukaryotic host cell but may instead be used in an assortment of eukaryotic host cells. A variety of eukaryotic host cells are available from depositories such as the American Type Culture Collection (ATCC) and are suitable for use with the vectors of the present invention. The choice of a particular host cell depends to some extent on the particular expression vector used to drive expression of the human glutamate receptor-encoding nucleic acids of the present invention. Exemplary host cells suitable for use in the present invention are listed in Table II below:

TABLE II

| Host Cell | Origin | Source |
|---|---|---|
| HepG-2 | Human Liver Hepatoblastoma | ATCC HB 8065 |
| CV-1 | African Green Monkey Kidney | ATCC CCL 70 |
| LLC-MK$_2$ | Rhesus Monkey Kidney | ATCC CCL 7.1 |
| 3T3 | Mouse Embryo Fibroblasts | ATCC CCL 92 |
| CHO-K1 | Chinese Hamster Ovary | ATCC CCL 61 |
| HeLa | Human Cervix Epitheloid | ATCC CCL 2 |
| RPMI8226 | Human Myeloma | ATCC CCL 155 |
| H4IIEC3 | Rat Hepatoma | ATCC CCL 1600 |
| C127I | Mouse Fibroblast | ATCC CCL 1616 |
| HS-Sultan | Human Plasma Cell Plasmocytoma | ATCC CCL 1484 |
| BHK-21 | Baby Hamster Kidney | ATCC CCL 10 |

A preferred cell line employed in this invention is the widely available cell line AV12-664 (hereinafter referred to as "AV12"). This cell line is available from the American Type Culture Collection under the accession number ATCC CRL 9595. The AV12 cell line was derived by injecting a Syrian hamster in the scruff of the neck with human adenovirus 12 and then isolating and culturing cells from the resulting tumor.

Cell lines, such as AV12, produce glutamate endogenously. As a result, substantial amounts of glutamate are secreted into the culture medium thereby making it somewhat difficult to express and study glutamate receptors due to the activation of the transfected receptor. Mechanisms such as the use of an effective glutamate transport system can be employed to remove excess glutmate effectively.

Therefore, a more preferred cell line for use in the present invention is the cell line RGT-18 (hereinafter referred to as "RGT"). The RGT cell line is constructed by transfecting the cell line AV12 with an expression plasmid in which the rat glutamate transporter gene (GLAST) is expressed. By using this cell line, the glutamate level in 24 hour medium of RGT is reduced to less than 3 micromolar, thus reducing the basal activation and/or desensitization of the receptor or the requirement for extensive washing to remove residual glutamate before assay procedures. See Storck, et al, *Proc. Nat'l Acad. Sci.USA,* 89:10955–59 (November 1992) and Desai et al, *Molecular Pharmacology,* 48:648–657 (1995).

A wide variety of vectors, some of which are discussed below, exist for the transformation of such mammalian host cells, but the specific vectors described herein are in no way intended to limit the scope of the present invention.

The pSV2-type vectors comprise segments of the simian virus 40 (SV40) genome that constitute a defined eukaryotic transcription unit-promoter, intervening sequence, and polyadenylation site. In the absence of the SV40 T antigen, the plasmid pSV2-type vectors transform mammalian and other eukaryotic host cells by integrating into the host cell chromosomal DNA. A large number of plasmid pSV2-type vectors have been constructed, such as plasmid pSV2-gpt, pSV2-neo, pSV2-dhfr, pSV2-hyg, and pSV2-β-globin, in which the SV40 promoter drives transcription of an inserted gene. These vectors are suitable for use with the coding sequences of the present invention and are widely available from sources such as the ATCC or the Northern Regional Research Laboratory (NRRL), 1815 N. University Street, Peoria, Ill., 61604.

The plasmid pSV2-dhfr (ATCC 37146) comprises a murine dihydrofolate reductase (dhfr) gene under the control of the SV40 early promoter. Under the appropriate conditions, the dhfr gene is known to be amplified, or copied, in the host chromosome. This amplification can result in the amplification of closely-associated DNA sequences and can, therefore, be used to increase production of a protein of interest. See. e.a., J. Schimke, *Cell,* 35:705–713 (1984).

Plasmids constructed for expression of the proteins of the present invention in mammalian and other eukaryotic host cells can utilize a wide variety of promoters. The present invention is in no way limited to the use of the particular promoters exemplified herein. Promoters such as the SV40 late promoter, promoters from eukaryotic genes, such as, for example, the estrogen-inducible chicken ovalbumin gene, the interferon genes, the gluco-corticoid-inducible tyrosine aminotransferase gene, and the thymidine kinase gene, and the major early and late adenovirus genes can be readily isolated and modified to express the genes of the present invention. Eukaryotic promoters can also be used in tandem to drive expression of a coding sequence of this invention. Furthermore, a large number of retroviruses are known that infect a wide range of eukaryotic host cells. The long terminal repeats in the retroviral DNA frequently encode functional promoters and, therefore, may be used to drive expression of the nucleic acids of the present invention.

Plasmid pRSVcat (ATCC 37152) comprises portions of a long terminal repeat of the Rous Sarcoma virus, a virus known to infect chickens and other host cells. This long terminal repeat contains a promoter which is suitable for use in the vectors of this invention. H. Gorman, et al., *Proceedings of the National Academy of Sciences (USA),* 79:6777 (1982). The plasmid pMSVi (NRRL B-1592) comprises the long terminal repeats of the Murine Sarcoma virus, a virus known to infect mouse and other host cells. The mouse metallothionein promoter has also been well characterized for use in eukaryotic host cells and is suitable for use in the expression of the nucleic acids of the present invention. The mouse metallothionein promoter is present in the plasmid pdBPV-MMTneo (ATCC 37224) which can serve as the starting material of other plasmids of the present invention.

One suitable expression vector system employs one of a series of vectors containing the BK enhancer, an enhancer derived from the BK virus, a human papovavirus. The preferred such vector systems are those which employ not only the BK enhancer but also the adenovirus-2-early region 1A(E1A) gene product. The E1A gene product (actually, the E1A gene produces two products, which are collectively referred to herein as "the E1A gene product") is an immediate-early gene product of adenovirus, a large DNA virus.

A preferred expression vector employed in the present invention is the phd series of vectors which comprise a BK enhancer in tandem with the adenovirus late promoter to drive expression of useful products in eukaryotic host cells. The construction and method of using the phd plasmid, as well as related plasmids, are described in U.S. Pat. No. 5,242,688, issued Sep. 7, 1993, and U.S. Pat. No. 4,992,373, issued Feb. 12, 1991, as well as co-pending U.S. patent application Ser. No. 07/368,700 and EPO Publication Number 245 949, published on Nov. 19, 1987, all of which are herein incorporated by reference. *Escherichia coli* K12 GM48 cells harboring the plasmid phd are available as part of the permanent stock collection of the Northern Regional Research Laboratory under accession number NRRL B-18525. The plasmid may be isolated from this culture using standard techniques.

The plasmid phd contains a unique BclI site which allows for the insertion of the gene encoding the protein of interest. The skilled artisan understands that linkers or adapters may be employed in cloning the gene of interest into this BclI site.

An even more preferred expression vector is the plasmid pGT-h. The pGT-h plasmid contains a unique BclI site which allows for the insertion of a gene encoding the protein of interest and also contains a gene encoding the hygromycin resistance determinant. The skilled artisan understands that linkers or adapters may be employed in cloning the gene of interest into this BclI site. Plasmid pGT-h contains the following elements beginning at the EcoR1 site and proceeding counterclockwise: the EcoR1 to blun-tended NdeI fragment of pBR322 containing the ampicillin resistant gene and origin of replication; the PvuII to blunt-ended BamHI fragment of pSV2-hyg' [derivative of pSV2-hyg constructed by A. Smith and P. Berg] containing a hygromycin phosphotransferase (HyPR) expression cistron; the blunt-ended NdeI(nt 2297) to AccI (nt 2246) restriction fragment of pBR322; the AccI (nt 4339) to StuI (nt 5122) restriction fragment of BKV-P2; the GBMT HindIII promoter cassette; HindIII and BclI linker; the 610 bp MhoI fragment of simian virus 40 (SV40) containing a splice junction; the 988 bp BclI to EcoRI fragment of SV40 containing the polyadenylation signal. See Berg, et al, *Biotechniques,* 14:972–978 (1993).

The pGT-h series of plasmids functions most efficiently when introduced into a host cell which produces the E1A gene product, cell lines such as AV12-664, RGT-18, 293 cells, and others, described supra. The construction and method of using the pGT-h plasmid is described in detail in Berg et al., supra, European Patent Application Publication 0445939 published on Sep. 11, 1991 and U.S. patent application Ser. No. 08/446,126, filed May 19, 1995, incorporated herein by reference. Plasmid pGT-h can be isolated from *E. coli* K12 AG1/pGT-h, which is deposited with the Northern Regional Research Laboratory under accession number NRRL B-18592.

Transfection of the mammalian cells with vectors can be performed by any of the known processes including, but not limited to, the protoplast fusion method, the calcium phosphate co-precipitation method, electroporation and the like. See, e.g., J. Sambrook, et al., supra, at 3:16.30–3:16.66.

Other routes of production are well known to skilled artisans. In addition to the plasmids discussed above, it is well known in the art that some viruses are also appropriate vectors. For example, the adenoviruses, the adeno-associated viruses, the vaccinia virus, the herpes viruses, the baculoviruses, and the rous sarcoma virus are useful. Such a method is described in U.S. Pat. No. 4,775,624, incorporated herein by reference. Several alternate methods of expression are also described in J. Sambrook, et al., supra, at 16.3–17.44.

In addition to prokaryotes and mammalian host cells, eukaryotic microbes such as yeast cultures may also be used. The imperfect fungus *Saccharomyces cerevisiae,* or common baker's yeast, is the most commonly used eukaryotic microorganism, although a number of other strains are commonly available. For expression in Saccharomyces sp., the plasmid YRp7 (ATCC-40053), for example, is commonly used. See, e.g., L. Stinchcomb, et al., *Nature,* 282:39 (1979); J. Kingsman et al., *Gene,* 7:141 (1979); S. Tschemper et al., *Gene,* 10:157 (1980). This plasmid already contains the trp gene which provides a selectable marker for a mutant strain of yeast lacking the ability to grow in tryptophan.

Suitable promoting sequences for use with yeast hosts include the promoters for 3-phosphoglycerate kinase [found on plasmid pAP12BD (ATCC 53231) and described in U.S. Pat. No. 4,935,350, issued Jun. 19, 1990, herein incorporated by reference] or other glycolytic enzymes such as enolase [found on plasmid pAC1 (ATCC 39532)], glyceraldehyde-3-phosphate dehydrogenase [derived from plasmid pHcGAPC1 (ATCC 57090, 57091)], hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase, as well as the alcohol dehydrogenase and pyruvate decarboxylase genes of *Zymomonas mobilis* (U.S. Pat. No. 5,000,000 issued Mar. 19, 1991, herein incorporated by reference).

Other yeast promoters, which are inducible promoters, having the additional advantage of their transcription being controllable by varying growth conditions, are the promoter regions for alcohol dehydrogenase 2, isocytochrome C, acid phosphatase, degradative enzymes associated with nitrogen metabolism, metallothionein [contained on plasmid vector pCL28XhoLHBPV (ATCC 39475) and described in U.S. Pat. No. 4,840,896, herein incorporated by reference], glyceraldehyde 3-phosphate dehydrogenase, and enzymes responsible for maltose and galactose [e.g. GAL1 found on plasmid pRY121 (ATCC 37658)] utilization. Suitable vectors and promoters for use in yeast expression are further described in R. Hitzeman et al., European Patent Publication No. 73,657A. Yeast enhancers such as the UAS Gal from *Saccharomyces cerevisiae* (found in conjunction with the CYC1 promoter on plasmid YEpsec—hI1beta ATCC 67024), also are advantageously used with yeast promoters.

Practitioners of this invention realize that, in addition to the above-mentioned expression systems, the cloned cDNA may also be employed in the production of transgenic animals in which a test mammal, usually a mouse, in which expression or overexpression of the proteins of the present invention can be assessed. The nucleic acids of the present invention may also be employed in the construction of "knockout" animals in which the expression of the native cognate of the gene is suppressed.

Skilled artisans also recognize that some alterations of SEQ ID NO:2 will fail to change the function of the amino acid compound. For instance, some hydrophobic amino acids may be exchanged for other hydrophobic amino acids. Those altered amino acid compounds which confer substantially the same function in substantially the same manner as the exemplified amino acid compound are also encompassed within the present invention. Typical such conservative substitutions attempt to preserve the: (a) secondary or tertiary structure of the polypeptide backbone; (b) the charge or hydrophobicity of the residue; or (c) the bulk of the side chain. Some examples of such conservative substitutions of amino acids, resulting in the production of proteins which may be functional equivalents of the protein of SEQ ID NO:2 are shown in Table III below:

TABLE III

| Original Residue | Exemplary Substitutions |
| --- | --- |
| Ala | Ser, Gly |
| Arg | Lys |
| Asn | Gln, His |
| Asp | Glu |
| Cys | Ser |
| Gln | Asn |
| Glu | Asp |
| Gly | Pro, Ala |
| His | Asn, Gln |
| Ile | Leu, Val |
| Leu | Ile, Val |
| Lys | Arg, Gln, Glu |
| Mel | Leu, Ile |
| Phe | Met, Leu, Gyr |
| Ser | Thr |
| Thr | Ser |
| Trp | Tyr |
| Tyr | Trp, Phe |
| Val | Ile, Leu |

These substitutions may be introduced into the protein in a variety of ways, such as during the chemical synthesis or by chemical modification of an amino acid side chain after the protein has been prepared.

Alterations of the protein having a sequence which corresponds to the sequence of SEQ ID NO:2 may also be induced by alterations of the nucleic acid compounds which encodes these proteins. These mutations of the nucleic acid compound may be generated by either random mutagenesis techniques, such as those techniques employing chemical mutagens, or by site-specific mutagenesis employing oligonucleotides. Those nucleic acid compounds which confer substantially the same function in substantially the same manner as the exemplified nucleic acid compounds are also encompassed within the present invention.

Other embodiments of the present invention are nucleic acid compounds which comprise isolated nucleic acid sequences which encode SEQ ID NO:2. As skilled artisans will recognize, the amino acid compounds of the invention can be encoded by a multitude of different nucleic acid sequences because most of the amino acids are encoded by more than one nucleic acid triplet due to the degeneracy of the amino acid code. Because these alternative nucleic acid sequences would encode the same amino acid sequences, the present invention further comprises these alternate nucleic acid sequences.

The gene encoding the human glutamate mGluR8 receptor molecule may be produced using synthetic methodology. This synthesis of nucleic acids is well known in the art. See. e.a., E. L. Brown, R. Belagaje, M. J. Ryan, and H. G. Khorana, *Methods in Enzymology,* 68:109–151 (1979). The DNA segments corresponding to the receptor gene are generated using conventional DNA synthesizing apparatus such as the Applied Biosystems Model 380A or 380B DNA synthesizers (commercially available from Applied Biosystems, Inc., 850 Lincoln Center Drive, Foster City, Calif. 94404) which employ phosphoramidite chemistry. In the alternative, the more traditional phosphotriester chemistry may be employed to synthesize the nucleic acids of this invention. [See. e.g., M. J. Gait, ed., *Oligonucleotide Synthesis. A Practical Approach,* (1984).]

The synthetic human glutamate mGluR8 receptor gene may be designed to possess restriction endonuclease cleavage sites at either end of the transcript to facilitate isolation from and integration into expression and amplification plasmids. The choice of restriction sites are chosen so as to properly orient the coding sequence of the receptor with control sequences to achieve proper in-frame reading and expression of the mGluR8 receptor molecule. A variety of other such cleavage sites may be incorporated depending on the particular plasmid constructs employed and may be generated by techniques well known in the art.

In an alternative methodology, the desired DNA sequences can be generated using the polymerase chain reaction as described in U.S. Pat. No. 4,889,818, which is herein incorporated by reference.

In addition to the deoxyribonucleic acid of SEQ ID NO:1, this invention also provides ribonucleic acids (RNA) which comprise the RNA sequence:

```
UGCUGUGUUG CAAGAAUAAA CUUUGGGUCU UCCAUUGCAA UACCACCUGU GGAGAAAAUG    60
GUAUGCGAGG GAAAGCGAUC AGCCUCUUGC CCUUGUUUCU UCCUCUUGAC CGCCAAGUUC   120
UACUGGAUCC UCACAAUGAU GCAAAGAACU CACAGCCAGG AGUAUGCCCA UUCCAUACGG   180
GUGGAUGGGG ACAUUAUUUU GGGGGGUCUC UUCCCUGUCC ACGCAAAGGG AGAGAGAGGG   240
GUGCCUUGUG GGGAGCUGAA GAAGGAAAAG GGGAUUCACA GACUGGAGGC CAUHCUUUAU   300
GCAAUUGACC AGAUUAACAA GGACCCUGAU CUCCUUUCCA ACAUCACUCU GGGUGUCCGC   360
AUCCUCGACA CGUGCUCUAG GGACACCUAU GCUUUGGAGC AGUCUCUAAC AUUCGUGCAG   420
GCAUUAAUAG AGAAAGAUGC UUCGGAUGUG AAGUGUGCUA AUGGAGAUCC ACCCAUUUUC   480
ACCAAGCCCG ACAAGAUUUC UGGCGUCAUA GGUGCUGCAG CAAGCUCCGU GUCCAUCAUG   540
GUUGCUAACA UUUUAAGACU UUUUAAGAUA CCUCAAAUCA GCUAUGCAUC CACAGCCCCA   600
GAGCUAAGUG AUAACACCAG GUAUGACUUU UUCUCUCGAG UGGUUCCGCC UGACUCCUAC   660
CAAGCCCAAG CCAUGGUGGA CAUCGUGACA GCACUGGGAU GGAAUUAUGU UUCGACACUG   720
GCUUCUGAGG GGAACUAUGG UGAGAGCGGU GUGGAGGCCU UCACCCAGAU CUCGAGGGAG   780
AUUGGUGGUG UUUGCAUUGC UCAGUCACAG AAAAUCCCAC GUGAACCAAG ACCUGGAGAA   840
UUUGAAAAAA UUAUCAAACG CCUGCUAGAA ACACCUAAUG CUCGAGCAGU GAUUAUGUUU   900
GCCAAUGAGG AUGACAUCAG GAGGAUAUUG GAAGCAGCAA AAAAACUAAA CCAAAGUGGG   960
CAUUUUCUCU GGAUUGGCUC AGAUAGUUGG GGAUCCAAAA UAGCACCUGU CUAUCAGCAA  1020
GAGGAGAUUG CAGAAGGGGC UGUGACAAUU UUGCCCAAAC GAGCAUCAAU UGAUGGAUUU  1080
GAUCGAUACU UUAGAAGCCG AACUCUUGCC AAUAAUCGAA GAAAUGUGUG GUUUGCAGAA  1140
UUCUGGGAGG AGAAUUUUGG CUGCAAGUUA GGAUCACAUG GGAAAAGGAA CAGUCAUAUA  1200
AAGAAAUGCA CAGGGCUGGA GCGAAUUGCU CGGGAUUCAU CUUAUGAACA GGAAGGAAAG  1260
GUCCAAUUUG UAAUUGAUGC UGUAUAUUCC AUGGCUUACG CCCUGCACAA UAUGCACAAA  1320
GAUCUCUGCC CUGGAUACAU UGGCCUUUGU CCACGAAUGA GUACCAUUGA UGGGAAAGAG  1380
GUACUUGGUU AUAUUCGGGC UGUAAAUUUU AAUGGCAGUG CUGGCACUCC UGUCACUUUU  1440
AAUGAAAACG GAGAUGCUCC UGGACGUUAU GAUAUCUUCC AGUAUCAAAU AACCAACAAA  1500
AGCACAGAGU ACAAAGUCAU CGGCCACUGG ACCAAUCAGC UUCAUCUAAA AGUGGAAGAC  1560
AUGCAGUGGG CUCAUAGAGA ACAUACUCAC CCGGCGUCUG UCUGCAGCCU GCCGUGUAAG  1620
CCAGGGGAGA GGAAGAAAAC GGUGAAAGGG GUCCCUUGCU GCUGGCACUG UGAACGCUGU  1680
GAAGGUUACA ACUACCAGGU GGAUGAGCUG UCCUGUGAAC UUGCCCUCU GGAUCAGAGA  1740
CCCAACAUGA ACCGCACAGG CUGCCAGCUU AUCCCCAUCA UCAAAUUGGA GUGGCAUUCU  1800
CCCUGGGCUG UGGUGCCUGU GUUUGUUGCA AUAUUGGGAA UCAUCGCCAC CACCUUUGUG  1860
```

-continued

```
AUCGUGACCU UUGUCCGCUA UAAUGACACA CCUAUCGUGA GGGCUUCAGG ACGCGAACUU    1920

AGUUACGUGC UCCUAACGGG GAUUUUUCUC UGUUAUUCAA UCACGUUUUU AAUGAUUGCA    1980

GCACCAGAUA CAAUCAUAUG CUCCUUCCGA CGGGUCUUCC UAGGACUUGG CAUGUGUUUC    2040

AGCUAUGCAG CCCUUCUGAC CAAAACAAAC CGUAUCCACC GAAUAUUUGA GCAGGGGAAG    2100

AAAUCUGUCA CAGCGCCCAA GUUCAUUAGU CCAGCAUCUC AGCUGGUGAU CACCUUCAGC    2160

CUCAUCUCCG UCCAGCUCCU UGGAGUGUUU GUCUGGUUUG UUGUGGAUCC CCCCCACAUC    2220

AUCAUUGACU AUGGAGAGCA GCGGACACUA GAUCCAGAGA AGGCCAGGGG AGUGCUCAAG    2280

UGUGACAUUU CUGAUCUCUC ACUCAUUUGU UCACUUGGAU ACAGUAUCCU CUUGAUGGUC    2340

ACUUGUACUG UUUAUGCCAA UAAAACGAGA GGUGUCCCAG AGACUUUCAA UGAAGCCAAA    2400

CCUAUUGGAU UUACCAUGUA UACCACCUGC AUCAUUUGGU UAGCUUUCAU CCCCAUCUUU    2460

UUUGGUACAG CCCAGUCAGC AGAAAAGAUG UACAUCCAGA CAACAACACU UACUGUCUCC    2520

AUGAGUUUAA GUGCUUCAGU AUCUCUGGGC AUGCUCUAUA UGCCCAAGGU UUAUAUUAUA    2580

AUUUUUCAUC CAGAACAGAA UGUUCAAAAA CGCAAGAGGA GCUUCAAGGC UGUGGUGACA    2640

GCUGCCACCA UGCAAAGCAA ACUGAUCCAA AAAGGAAAUG ACAGACCAAA UGGCGAGGUG    2700

AAAAGUGAAC UCUGUGAGAG UCUUGAAACC AACACUUCCU CUACCAAGAC AACAUAUAUC    2760

AGUUACAGCA AUCAUUCAAU CUGAAACAGG GAAAUGGCAC AAUCUGAAGA GACGUGGUAU    2820

AUGAUCUUAA AUGAUGAACA UGAGACCGCA AAAAUUCACU CCUGGAGAUC UCCGUAGACU    2880

ACAAUCAAUC AAAUCAAUAG UCAGUCUUGU AAGGAACAAA AAUUAGCCAU GAGCCAAAAG    2940

UAUCAAUAAA CGGGGAGUGA AGAAACCCGU UUUAUACAAU AAAACCAAUG AGUGUCAAGC    3000

UAAAGUAUUG CUUAUUCAUG AGCAGUUAAA ACAAAUCACA AAAGGAAAAC UAAUGUUAGC    3060

UCGUGAAAAA AAUGCUGUUG AAAUAAAUAA UGUCUGAUGU UAUUCUUGUA UUUUUCUGUG    3120

AUUGUGAGAA CUCCCGUUCC UGUCCCACAU UGUUUAACUU GUAUAAGACA AUGAGUCUGU    3180

UUCUUGUAAU GGCUGACCAG AUUGAAGCCC UGGGUUGUGC UAAAAAUAAA UGCAAUGAUU    3240

GAUGCAUGCA AUUUUUUAUA CAAAUAAUUU AUUUCUAAUA AUAAAGGAAU CUUUUGCAAA    3300

AAAAAAAAAA AAAAACUCGA G                                             3321
``` which is hereinafter referred to as SEQ ID NO:3, or the complementary ribonucleic acid, or a fragment of either SEQ ID NO:3 or the complement thereof. Preferably, the ribonucleic acid is a compound encompassing nucleotides 58 through 2781 of SEQ ID NO:3. The ribonucleic acids of the present invention may be prepared using the polynucleotide sysnthetic methods discussed supra or they may be prepared enzymatically using RNA polymerases to transcribe a DNA template.

Preferred systems for preparing the ribonucleic acids of the present invention employ the RNA polymerase from the bacteriophage T7 or the bacteriophage SP6. Both of these RNA polymerases are highly specific and require the insertion of bacteriophage-specific sequences at the 5' end of the message to be read. See, J. Sambrook, et al., supra, at 18.82–18.84.

The present invention also provides nucleic acids, RNA or DNA, which are complementary to SEQ ID NO:1, nucleotides 58 through 2781 of SEQ ID NO:1, SEQ ID NO: 3, or nucleotides 58 through 2781 of SEQ ID NO:3.

The present invention also provides probes and primers useful for molecular biology techniques. A compound which encodes for SEQ ID NO:1, nucleotides 58 through 2781 of SEQ ID NO:1, SEQ ID NO:3, nucleotides 58 through 2781 of SEQ ID NO:3 or a complementary sequence of SEQ ID NO:1, nucleotides 58 through 2781 of SEQ ID NO:1, SEQ ID NO:3 or nucleotides 58 through 2781 of SEQ ID NO:3, or a fragment thereof, and which is at least 18 base pairs in length, and which will selectively hybridize to human genomic DNA or messenger RNA encoding a human glutamate receptor, is provided. Preferably, the 18 or more base pair compound is DNA.

The term "selectively hybridize" as used herein may refer to either of two situations. In the first such embodiment of this invention, the nucleic acid compounds described supra hybridize to a human glutamate receptor under more stringent hybridization conditions than these same nucleic acid compounds would hybridize to an analogous glutamate receptor of another species, e.g. rodent. In the second such embodiment of this invention, these probes hybridize to the mGluR8 receptor under more stringent hybridization conditions than other related compounds, including nucleic acid sequences encoding other glutamate receptors.

These probes and primers can be prepared enzymatically as described supra. In one preferred embodiment, these probes and primers are synthesized using chemical means as described supra. Probes and primers of defined structure may also be purchased commercially.

The present invention also encompasses recombinant DNA cloning vectors and expression vectors comprising the nucleic acids of the present invention. Many of the vectors encompassed within this invention are described above. The preferred nucleic acid vectors are those which are DNA. A preferred recombinant DNA vector comprises the isolated DNA sequence SEQ ID NO:1. The most preferred comprises nucleotides 58 through 2781 of SEQ ID NO:1. Plasmid pGT-h is an especially preferred DNA vector of the present invention.

The skilled artisan understands that the type of cloning vector or expression vector employed depends upon the availability of appropriate restriction sites, the type of host cell in which the vector is to be transfected or transformed, the purpose of the transfection or transformation (e.g., transient expression in an oocyte system, stable transformation as an extrachromosomal element, or integration into the host chromosome), the presence or absence of readily assayable markers (e.g., antibiotic resistance markers, metabolic markers, or the like), and the number of copies of the gene to be present in the cell.

The type of vector employed to carry the nucleic acids of the present invention may be RNA viruses, DNA viruses, lytic bacteriophages, lysogenic bacteriophages, stable bacteriophages, plasmids, viroids, and the like. The most preferred vectors of the present invention are those derived from plasmids.

When preparing an expression vector the skilled artisan understands that there are many variables to be considered. One such example is the use of a constitutive promoter, i.e. a promoter which is functional at all times, instead of a regulatable promoter which may be activated or inactivated by the artisan using heat, addition or removal of a nutrient, addition of an antibiotic, and the like. The practitioner also understands that the amount of nucleic acid or protein to be produced dictates, in part, the selection of the expression system. For experiments examining the amount of the protein expressed on the cell membrane or for experiments examining the biological function of an expressed membrane protein, for example, it may be unwise to employ an expression system which produces too much of the protein. The addition or subtraction of certain sequences, such as a signal sequence preceding the coding sequence, may be employed by the practitioner to influence localization of the resulting polypeptide. Such sequences added to or removed from the nucleic acid compounds of the present invention are encompassed within this invention.

The plasmid of the present invention can be readily modified to construct expression vectors that produce mGluR8 receptors in a variety of organisms, including, for example, *E. coli,* Sf9 (as host for baculovirus), Spodoptera and Saccharomyces.

One of the most widely employed techniques for altering a nucleic acid sequence is by way of oligonucleotide-directed site-specific mutagenesis. B. Comack, "Current Protocols in Molecular Biology", 8.01–8.5.9, (F. Ausubel, et al., eds. 1991). In this technique an oligonucleotide, whose sequence contains the mutation of interest, is synthesized as described supra. This oligonucleotide is then hybridized to a template containing the wild-type sequence. In a most preferred embodiment of this technique, the template is a single-stranded template. Particularly preferred are plasmids which contain regions such as the f1 intergenic region. This region allows the generation of single-stranded templates when a helper phage is added to the culture harboring the "phagemid".

After the annealing of the oligonucleotide to the template, a DNA-dependent DNA polymerase is then used to synthesize the second strand from the oliognucleotide, complementary to the template DNA. The resulting product is a heteroduplex molecule containing a mismatch due to the mutation in the oligonucleotide. After DNA replication by the host cell a mixture of two types of plasmid are present, the wild-type and the newly constructed mutant. This technique permits the introduction of convenient restriction sites such that the coding sequence may be placed immediately adjacent to whichever transcriptional or translational regulatory elements are employed by the practitioner.

The construction protocols utilized for *E. coli* can be followed to construct analogous vectors for other organisms, merely by substituting, if necessary, the appropriate regulatory elements using techniques well known to skilled artisans.

Host cells which harbor the nucleic acids provided by the present invention are also provided. A preferred host cell is an Xenopus sp. oocyte which has been injected with RNA or DNA compounds of the present invention. Most preferred oocytes of the present invention are those which harbor a sense mRNA of the present invention. Other preferred host cells include AV12, RGT-18 and *E. coli* cells which have been transfected and/or transformed with a vector which comprises a nucleic acid of the present invention.

The present invention also provides a method for constructing a recombinant host cell capable of expressing SEQ ID NO:2, said method comprising transforming a host cell with a recombinant DNA vector that comprises an isolated DNA sequence which encodes SEQ ID NO:2. The preferred host cell is RGT-18. The preferred vector for expression is one which comprises SEQ ID NO:1, more preferably nucleotides 58 through 2781 of SEQ ID NO:1. Another suitable host cell for this method is *E. coli.* A preferred expression vector in *E. coli* is one which comprises SEQ ID NO:1, more preferably nucleotides 58 through 2781 of SEQ ID NO:1. Transformed host cells may be cultured under conditions well known to skilled artisans such that SEQ ID NO:2 is expressed, thereby producing mGluR8 in the recombinant host cell.

The ability of glutamate to bind to the mGluR8 receptor is essential in the development of a multitude of indications. In developing agents which act as antagonists or agonists of the mGluR8 receptor, it would be desirable, therefore, to determine those agents which bind the mGluR8 receptor. Generally, such an assay includes a method for determining whether a substance is a functional ligand of the mGluR8 receptor, said method comprising contacting a functional compound of the mGluR8 receptor with said substance, monitoring binding activity by physically detectable means, and identifying those substances which effect a chosen response. Preferably, the physically detectable means is competition with labeled glutamate or binding of ligand in an oocyte transient expression system The instant invention provides such a screening system useful for discovering agents which compete with glutamate for binding to the mGluR8 receptor, said screening system comprising the steps of:

a) preparing a human mGluR8 receptor;
b) exposing said human mGluR8 receptor to a potential inhibitor or surrogate of the glutamate/mGluR8 receptor complex;
c) introducing glutamate;
d) removing non-specifically bound molecules; and
e) quantifying the concentration of bound potential inhibitor and/or glutamate.

This allows one to rapidly screen for inhibitors or surrogates of the formation of the glutamate/mGluR8 receptor complex. Utilization of the screening system described above provides a sensitive and rapid means to determine compounds which interfere with the formation of the glutamate/mGluR8 receptor complex. This screening system may also be adapted to automated procedures such as a PANDEX® (Baxter-Dade Diagnostics) system allowing for efficient high-volume screening of potential therapeutic agents.

In such a screening protocol a mGluR8 receptor is prepared as elsewhere described herein, preferably using recombinant DNA technology. A sample of a test compound is then introduced to the reaction vessel containing the mGluR8 receptor followed by the addition of glutamate. In the alternative the glutamate may be added simultaneously with the test compound. Unbound molecules are washed free and the eluent inspected for the presence of glutamate or the test compound.

For example, in a preferred method of the invention, radioactively or chemically labeled glutamate may be used. The eluent is then scored for the chemical label or radioactivity. The absence or diminution of the chemical label or radioactivity indicates the formation of the glutamate/mGluR8 receptor complex. This indicates that the test compound has not effectively competed with glutamate in the formation of the glutamate/mGluR8 receptor complex. The presence of the chemical label or radioactivity indicates that the test compound has competed with glutamate in the formation of the glutamate/mGluR8 receptor complex. Similarly, a radioactively or chemically labeled test compound may be used in which case the same steps as outlined above would be used except that the interpretation of results would be the converse of using radioactively or chemically labelled glutamate.

As would be understood by the skilled artisan, these assays may also be performed such that the practitioner measures the radioactivity or chemical label remaining with the protein, not in the eluent. A preferred such assay employs radiolabeled glutamate. After the competition reaction has been performed the reaction mixture is then passed through a filter, the filter retaining the receptor and whatever is complexed with the receptor. The radioactivity on each filter is then measured in a scintillation counter. In such an assay higher amounts of radiolabel present indicate lower affinity for the receptor by the test compound.

The mGluR8 receptor may be free in solution or bound to a membrane. Whether the mGluR8 receptor is bound to a membrane or is free in solution, it is generally important that the conformation of the protein be conserved. In a preferred practice of the invention, therefore, the mGluR8 receptor is suspended in a hydrophobic environment employing natural or synthetic detergents, membrane suspensions, and the like. Preferred detergent complexes include the zwitterionic detergent 3-[(3-cholamidopropyl)-dimethylammonio]-1-propane sulfonate ("CHAPS" ) as well as sodium deoxycholate.

Skilled artisans will recognize that desirable dissociation constant ($K_i$) values are dependent on the selectivity of the compound tested. For example, a compound with a $K_i$ which is less than 10 nM is generally considered an excellent candidate for drug therapy. However, a compound which has a lower affinity, but is selective for the particular receptor, may be an even better candidate. The present invention, however, provides radiolabeled competition assays, whether results therefrom indicate high affinity or low affinity to mGluR8 receptor, because skilled artisans will recognize that any information regarding binding or selectivity of a particular compound is beneficial in the pharmaceutical development of drugs.

In one such competition assay, a battery of known glutamate receptor antagonists, agonists, and partial agonists are evaluated for their relative abilities to inhibit the binding of [$^3$H]glutamate to the human mGluR8 receptor of the present invention.

In this assay cells stably expressing the cloned human mGluR8 receptor are harvested by centrifugation at 2200×g for 15minutes at 4_C. Membranes for the binding assays are prepared by vortexing the cell pellet in 50 mM Tris.HCl, pH 7.4 ($0.5\times10^9$ cells/30 ml). The tissue suspension is then centrifuged at 39,800×g for 10 minutes at 4_C. This procedure is repeated for a total of three washes, with a 10 minute incubation at 37_C. between the second and third washes. The final pellet is homogenized in 67 mM Tris.HCl, pH 7.4, at $12.5\times10^6$ cells/ml using a TISSUMIZER® (Tekmar, Cincinnati, Ohio) at setting 65 for 15 seconds.

Binding assays are performed in triplicate in 0.8 ml total volume. Volumes of 200 μl of membrane suspension (0.07–0.10 mg of protein) and 200 μl of drug dilution in water are added to 400 μl of 67 mM of Tris.HCl, pH 7.4, containing [$^3$H]glutamate (35 nM final concentration, 23.7 Ci/mole), calcium chloride (3 mM), pargyline (10 μM), and L-ascorbic acid (5.7 nM). The reaction mixtures are incubated at 37_C. for 15 minutes and then rapidly filtered, using a BRANDEL™ cell harvester (Model MB-48R; Brandel, Gaithersburg, Md.) over Whatman GF/B filters that had been presoaked in 0.5% polyethyleneimine and pre-cooled with ice-cold 50 mM Tris.HCl, pH 7.4. The filters are then washed rapidly times with ice-cold (4×1 ml each).

The amount of [$^3$H]glutamate trapped on the filters is determined by liquid scintillation counting. For the competition experiments, six concentrations of displacing drugs are used, ranging from $10^{-5}$ to $10^{-10}$ M. The $IC_{50}$ values are determined by nonlinear regression analysis (SYSTAT™; Systat Inc., Evanston, Ill.) which may be converted to $K_i$ values using the Cheng-Prusoff equation. Y. Cheng and W. H. Prusoff, *Biochemical Pharmacology,* 22:3099–3108 (1973).

In this particular type of competition assay the following compounds are frequently used.

(a) Quisqualate—a compound of the formula

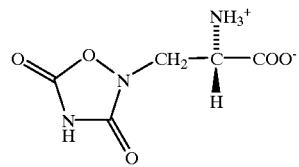

having the chemical name (S)-α-amino-3,5-dioxo-1,2,4-oxadiazolidine-2-propanoate. This compound can be prepared as described in J. E. Baldwin, et al., *Chemical Communications,* 256 (1985).

(b) Glutamate—a compound of the formula

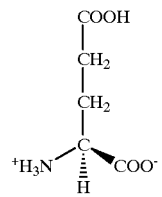

having the chemical name 1-aminopropane-1,3-dicarboxylic acid. This compound is readily available and can be purchased commercially from several sources.

(c) Ibotenate—a compound of the formula

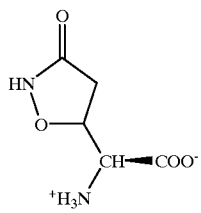

having the chemical name α-amino-3-hydroxy-5-isoxazoleacetate, which can be prepared as described in U.S. Pat. No. 3,459,862, herein incorporated by reference.

(d) t-ACPD—a compound of the formula

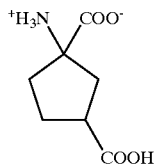

having the chemical name 1-aminocyclopentane-1,3-dicarboxylic acid. This compound can be purchased commercially from several sources.

(e) (2R,4R) 4-amino-pyrrolidine-2,4-dicarboxylic acid, a compound of the formula

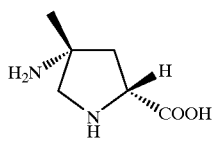

which is described in co-pending U.S. Pat. No. 5,473,077. Many 1-substituted derivatives of this dicarboxylic acid are also effective as mGluR8 antagonists.

The previously described screening system identifies compounds which competitively bind to the mGluR8 receptor. Determination of the ability of such compounds to stimulate or inhibit the action of the mGluR8 receptor is essential to further development of such compounds for therapeutic applications. The need for a bioactivity assay system which determines the response of the mGluR8 receptor to a compound is clear. The instant invention provides such a bioactivity assay, said assay comprising the steps of:
  a) transfecting a mammalian host cell with an expression vector comprising DNA encoding a mGluR8 receptor;
  b) culturing said host cell under conditions such that the mGluR8 receptor protein is expressed,
  c) exposing said host cell so transfected to a test compound, and
  d) measuring the change in a physiological condition known to be influenced by the binding of glutamate to the mGluR8 receptor relative to a control in which the transfected host cell is exposed to glutamate.

An oocyte transient expression system can be constructed according to the procedure described in S. Lübbert, et al., *Proceedings of the National Academy of Sciences (USA)*, 84:4332 (1987).

In an especially preferred embodiment of this invention an assay measuring the inhibition of forskolin-stimulated cAMP synthesis is performed. The inhibition of cAMP synthesis is known to positively correlated with the addition of glutamate to cells containing certain types of metabotropic receptors.

In another embodiment, this invention provides a method for identifying, in a test sample, DNA homologous to a probe of the present invention, wherein the test nucleic acid is contacted with the probe under hybridizing conditions and identified as being homologous to the probe. Hybridization techniques are well known in the art. See, e.g., J. Sambrook, et al., supra, at Chapter 11.

The nucleic acid compounds of the present invention may also be used to hybridize to genomic DNA which has been digested with one or more restriction enzymes and run on an electrophoretic gel. The hybridization of radiolabeled probes onto such restricted DNA, usually fixed to a membrane after electrophoresis, is well known in the art. See, e.g., J. Sambrook, supra. Such procedures may be employed in searching for persons with mutations in these receptors by the well-known techniques of restriction fragment length polymorphisms (RFLP), the procedures of which are described in U.S. Pat. No. 4,666,828, issued May 19, 1987, the entire contents of which is incorporated herein by reference.

The proteins of this invention as well as fragments of these proteins may be used as antigens for the synthesis of antibodies. The term "antibody" as used herein describes antibodies, fragments of antibodies (such as, but not limited, to Fab, Fab', $Fab_2$', and Fv fragments), and chimeric, humanized, veneered, resurfaced, or CDR-grafted antibodies capable of binding antigens of a similar nature as the parent antibody molecule from which they are derived. The instant invention also encompasses single chain polypeptide binding molecules.

The term "antibody" as used herein is not limited by the manner in which the antibodies are produced, whether such production is in situ or not. The term "antibody" as used in this specification encompasses those antibodies produced by recombinant DNA technology means including, but not limited, to expression in bacteria, yeast, insect cell lines, or mammalian cell lines.

The production of antibodies, both monoclonal and polyclonal, in animals, especially mice, is well known in the art. See. e.g., C. Milstein, *Handbook of Experimental Immunology*, (Blackwell Scientific Pub., 1986); J. Goding, *Monoclonal Antibodies: Principles and Practice*, (Academic Press, 1983). For the production of monoclonal antibodies the basic process begins with injecting a mouse, or other suitable animal, with an immunogen. The mouse is subsequently sacrificed and cells taken from its spleen are fused with myeloma cells, resulting in a hybridoma that reproduces in vitro. The population of hybridomas is screened to isolate individual clones, each of which secretes a single antibody species, specific for the immunogen. The individual antibody species obtained in this way is each the product of a single B cell from the immune animal generated in response to a specific antigenic site, or epitope, recognized on the immunogenic substance.

Chimeric antibodies are described in U.S. Pat. No. 4,816,567, which issued Mar. 28, 1989 to S. Cabilly, et al. This reference discloses methods and vectors for the preparation of chimeric antibodies. The entire contents of U.S. Pat. No. 4,816,567 are incorporated herein by reference. An alternative approach to production of genetically engineered antibodies is provided in U.S. Pat. No. 4,816,397, which also issued Mar. 28, 1989 to M. Boss, et al., the entire contents of which are incorporated herein by reference. The Boss patent teaches the simultaneous co-expression of the heavy and light chains of the antibody in the same host cell.

The approach of U.S. Pat. No. 4,816,397 has been further refined as taught in European Patent Publication No. 0 239 400, which published Sep. 30, 1987. The teachings of this European patent publication (Winter) are a preferred format for the genetic engineering of the reactive monoclonal antibodies of this invention. The Winter technology involves the replacement of complementarity determining regions (CDRs) of a human antibody with the CDRs of a murine monoclonal antibody thereby converting the specificity of the human antibody to the specificity of the murine antibody which was the source of the CDR regions. This "CDR grafting" technology affords a molecule containing minimal murine sequence and thus is less immunogenic.

Single chain antibody technology is yet another variety of genetically engineered antibody which is now well known in the art. See. e.g. R. E. Bird, et al., *Science* 242:423–426 (1988); PCT Publication No. WO 88/01649, which was published Mar. 10, 1988. The single chain antibody technology involves joining the binding regions of heavy and light chains with a polypeptide sequence to generate a single polypeptide having the binding specificity of the antibody from which it was derived.

The aforementioned genetic engineering approaches provide the skilled artisan with numerous means to generate molecules which retain the binding characteristics of the parental antibody while affording a less immunogenic format.

These antibodies are used in diagnostics, therapeutics or in diagnostic/therapeutic combinations. By "diagnostics" as used herein is meant testing that is related to either the in vitro or in vivo diagnosis of disease states or biological status in mammals, preferably in humans. By "therapeutics" and "therapeutic/diagnostic combinations" as used herein is respectively meant the treatment or the diagnosis and treatment of disease states or biological status by the in vivo administration to mammals, preferably humans, of the antibodies of the present invention. The antibodies of the present invention are especially preferred in the diagnosis and/or treatment of conditions associated with an excess or deficiency of mGluR8 receptors.

In addition to being functional as direct therapeutic and diagnostic aids, the availability of a family of antibodies which are specific for the mGluR8 receptor enables the development of numerous assay systems for detecting agents which bind to this receptor. One such assay system comprises radiolabeling mGluR8 receptor-specific antibodies with a radionuclide such as $^{125}I$ and measuring displacement of the radiolabeled mGluR8 receptor-specific antibody from solid phase mGluR8 receptor in the presence of a potential antagonist.

Numerous other assay systems are also readily adaptable to detect agents which bind mGluR8 receptor. Examples of these aforementioned assay systems are discussed in *Methods in Enzymology*, (J. Langone. and H. Vunakis, eds. 1981), Vol. 73, Part B, the contents of which are herein incorporated by reference. Skilled artisans are directed to Section II of *Methods in Enzymology*, Vol. 73, Part B, supra, which discusses labeling of antibodies and antigens, and Section IV, which discusses immunoassay methods.

In addition to the aforementioned antibodies specific for the mGluR8 receptor, this invention also provides antibodies which are specific for the hypervariable regions of the anti-mGluR8 receptor antibodies. Some such anti-idiotypic antibodies would resemble the original epitope, the mGluR8 receptor, and, therefore, would be useful in evaluating the effectiveness of compounds which are potential antagonists, agonists, or partial agonists of the mGluR8 receptor. See. e.g., Cleveland, et al., *Nature (London)*, 305:56 (1983); Wasserman, et al., *Proceedings of the National Academy of Sciences (USA)*, 79:4810 (1982).

In another embodiment, this invention encompasses pharmaceutical formulations for parenteral administration which contain, as the active ingredient, the anti-mGluR8 receptor antibodies described, supra. Such formulations are prepared by methods commonly used in pharmaceutical chemistry.

Products for parenteral administration are often formulated and distributed in solid, preferably freeze-dried form, for reconstitution immediately before use. Such formulations are useful compositions of the present invention. Their preparation is well understood by pharmaceutical chemists.

In general, these formulations comprise the active ingredient in combination with a mixture of inorganic salts, to confer isotonicity, as well as dispersing agents such as lactose, to allow the dried preparation to dissolve quickly upon reconstitution. Such formulations are reconstituted for use with highly purified water to a known concentration.

Alternatively, a water soluble form of the antibody can be dissolved in one of the commonly used intravenous fluids and administered by infusion. Such fluids include physiological saline, Ringer's solution or a 5% dextrose solution.

The following example more fully describes the present invention. Those skilled in the art will recognize that the particular reagents, equipment, and procedures described in the Example is merely illustrative and is not intended to limit the present invention in any manner.

EXAMPLE
I. Preparation of the RGT Cell Line

To construct the RGT cell line of the present invention, cDNA encoding the sodium dependent glutamate/asparate transporter (GLAST) was isolated from lambda ZAP® II cDNA library derived from rat hippocampus (Stratagene, Inc., La Jolla, Calif., Catalog # 936518). The published sequence (see Desai et al, supra) was used to design PCR primers which generated a 602 base pair fragment from an aliquot off the library as template. This fragment was used as template to generate a radioactively labelled probe for screening the cDNA library. Using standard plaque hybridization techniques (moderate stringency, 1 M $Na^+$, 60__C) a number of positive clones were isolated. By further dilution and hybridization, a phage clone was purified which contained the complete coding sequence for the gene. The plasmid containing the insert was excised from the phage using helper phage and protocols supplied by the manufacturer. The GLAST cDNA from this lambda ZAPII phage was excised on a pBluescript phagemid vector as described by Stratagene, Inc. (pBluescript® SK+).

The GLAST cDNA was removed from the phagemid on a 2.6 kb EcoRV-SmaI restriction fragment and XbaI linkers were added to each end. This fragment was introduced into the XbaI site of the mammalian expression vector pRc/RSV to construct pRS151 (Invitrogen, Catalog # V780-20). The GLAST cDNA was then transfected into the AV12 cell line using the $CaPO_4$ method (Graham et al, *Virology* 52:456–467, (1973)) with reagents obtained from Stragagene, Inc. Ten micrograms of plasmid were used without carrier DNA for each 10 cm petri plate of cells at approximately 50% confluancy. Clones expressing GLAST were selected by resistance to G418 (500 ug/ml)(GIBCO-BRL). Clone RGT was found to accumulate less than 3 micromolar glutamate in culture compared with parent AV12 at 100 micromolar after 24 hours growth.

II. Isolation and Characterization of the cDNA Encoding the Human MGLUR8 Gene A cDNA clone encoding the human mGluR8 was isolated from the human fetal retina cDNA library (commercially available from Stratagene, Inc. Lajolla, Calif., Catalog #93702) by hybridization with a $^{32}$p labeled human mGluR8 probe as follows:

A. Design of Primers and Preparation of $^{32}$P-labeled Human mGluR8 Probe

A computer-generated alignment of published amino acid and nucleotide sequences of mouse mGluR8 showed a number of highly homologous regions with other members of the mGluR family. These homologous regions were avoided in designing the primers for PCR amplification of fragments corresponding to the human mGluR8 gene. By using the human based codon usage file from Gene Bank [See R. Lathe et al., *J. Mol. Biol.*, 183:7–12 (1985), and also S. Aota et al., Nucleic Acids Res. 16: r315–402, (1988)], the ten degenerate oligonucleotides listed below were generated:

8P1:
  5'-TGSGAGGGMAAGMGSWSMACCWSNTGYCC-3' (SEQ ID NO:4)
8P2: 5'-ATGATGCARAGRACYCACAGCCARGA-3' (SEQ ID NO:5)
8P3: 5'-GTCKCCRTTRGCRACCTTCACRTC-3' (SEQ ID NO:6)
8P4: 5'-KGCRGCRCCKATSACRCCRSWRATYTTRTC-3' (SEQ ID NO:7)
8P5: 5'-WSMGGMWSMCAYGGSAAGAMGNCGNAA-3' (SEQ ID NO:8)
8P6: 5'-GTCYTCCACYTTYAGGTGMAGYTGRTT-3" (SEQ ID NO:9)
8P7:
  5'-SACRSWYGCKGGGTGSGTGTGCTCYCKRTT-3 (SEQ ID NO:10)
8P8: 5'-GCMCCYGACACMATCATCTGYWSYTT-3' (SEQ ID NO:11)
8P9: 5'-RSWRSWRGTGTTGGTYTCMAGRCT-3' (SEQ ID NO:12)
8P10: 5'-RTGRTCRCTGTAGCTGATGTAKGTKGT-3' (SEQ ID NO:13)

where R=A or G, Y=C or T, M=A or C, K=C or T, S=G or C, W=A or T, D=G or A or T and N=A or C or G or T These degenerate oligonucleotides were synthesized by the phosphoramidite method on a DNA Synthesizer (Applied Biosystems model 380B) and purified by polyacrylamide gel electrophoresis. For PCR amplifications, the oligonucleotides were paired in five combinations [(a) 8P1+8P3, (b) 8P1+8P4, (c) 8P2+8P4, (d) 8P5+8P7 and (e) 8P8+8P10] to generate approximately 405 bp, 457 bp, 384 bp, 505 bp and 808 bp DNA fragments corresponding to the human mGluR8 gene.

The first PCR reaction mixtures (50 μl) each contained; 10 μl of 5×PCR buffer [50 mM Tris-HCl (pH 8.5), 150 mM KCl, 15 mM MgCl$_2$ and 0.05% gelatin]; 10 μl of 2 mM dNTP mixture (dNTP=dATP+dTTP+dGTP+dCTP); 2 μl of Primer Mix (20 pmoles each); 2 μl of fetal retinal cDNA (Stratagene, Inc., Lajolla, Calif., Catalog #93702) as a template; 2.4 μl of Taq DNA Polymerase-Taq Start™ antibody mixture which is prepared by mixing 4.4 μl of Taq DNA polymerase (GIBCO/BRC) and 4.4 μl (7 μM) of TaqStart™ antibody (ClonTech Laboratories, Inc. Palo Alto, Calif. Catalog # 5400-1) with 17.6 μl of dilution buffer supplied by the vendor (ClonTech Laboratories, Inc.) and 25.6 μl of autoclaved distilled water. The content of each tube was mixed, overlaid with 50 μl of mineral oil and then incubated in a DNA thermal cycles 9600 (PerkinElmer, Norwalk, Conn.) at 95_C for 5 minutes. Amplification was performed by touch down PCR using the following conditions: 30 second denaturing at 94_C; 30 second annealing at 55° C. and 1 minute extension at 72° C. with acute decrease of 0.5° C. per cycle for a total of 20 cycles followed by 30 second denaturing at 94° C., 30 second annealing at 45° C.; and 1 minute extension at 72° C. for a total of 10 cycles. The incubation was continued at 72° C. for 7 minutes and the mixture was soaked at 4° C. until used.

A portion (1 μl) of this reaction mixture was used as a template for further amplification by second PCR using an appropriate pair of Primer Mix (8P2+8P3 for reaction (a), 8P1+8P3 for reaction (b), 8P2+8P3 for reaction (c), 8P5+8P6 for reaction (d) and 8P8+8P9 for reaction (e) described above respectively). The Second PCR reaction mixture (50 μl) each contained: 5 μl of 10×PCR (100 mM Tris-Hcl (pH 8.3), 500 mM KCl, 1.5 mM MgCl$_2$ and 0.01% gelatin, w/v); 2 μl of 2.5 μM nucleotide mixture containing DATP, dTTP, dCTP and dGTP; 2 μl of Primer Mix (20 pmoles each); 1 μl of reaction mixture from the first PCR; 0.25 μl (2.5 units) of Taq DNA Polymerase (GIBCO/BRL); and 39 μl of autoclaved distilled water. The amplification conditions were: 1 minute denaturing at 94° C.; 1 minute annealing at 53° C. and 2 minute extension at 72° C. for a total of 35 cycles.

The incubation was continued at 72° C. for 7 minutes. The sample was then maintained at 4° C. A portion (15 μl) of the reaction mixture was analyzed by agarose (1%) gel electrophoresis and the DNA bonds visualized by ethidium bromide staining.

Of the five Primer Pairs used, two oligonucleotide pairs (8P2+8P3 and 8P8+8P9) yielded approximately 332 bp and 762 bp fragments containing mGluR8 specific sequences. These fragments were subcloned into pCR-script®SK(+) plasmid (Stratagene, Inc., Lajolla, Calif.) at the SrfI restriction site according to the procedures recommended by the vendor. About 12 white transformates were picked. Each was grown in 3 mL TY media containing 100 μg/ml ampicillin. Plasmids were isolated from these culture using the QIAPrep Spin Plasmid Kit (Quiagen, Inc., Chattsworth, Calif., Catalog #27106) DNA sequence analysis of the insert confirmed the presence of human mGluR8 specific sequences in the amplified PCR product.

To prepare a $^{32}$p-labeled probe, the plasmid DNA containing the above PCR product was used as a template under the following conditions. The mixture (40 μl) contained: 4 μl of 10×PCR buffer (100 mM Tris-HCl (pH 8.3), 500 mM KCl, 1.5 mM MgCl$_2$ and 0.01% gelatin, w/v); 3 μl of 0.5 mM nucleotide mixture containing dATP, dTTP, and dGTP; 15 μl (150 μci) of [γ-$^{32}$P] dCTP (Dupont, NEN, Catalog #NEG013H); 2 μl of Primer Mix (8P2+8P3 or 8P8+8P9, 20 pmoles each); 1 μl of purified PCR amplification product, 0.25 μl of TAQ polymerase (GIBCO/BRL); and 75 μl of autoclaved distilled water. The amplification conditions were: 30 sec denaturing at 95° C.; 1 minute annealing at 55° C.; and 2 minutes extension at 72° C. for a total of 30 cycles. The incubation was continued at 72° C. for 7 minutes. The sample was then maintained at 4° C. The amplified radiolabeled probe was purified by a NUCTRAP® probe purification column (Stratagene, Inc., Lajolla, Calif., Catalog #400701) and stored at 4° C. until used.

B. Screening the cDNA Library

A human fetal retina cDNA library (λZAP®II, Stratagene Inc., Lajolla, Calif., Catalog #937202) consisting of 3.7×10$^6$ phages was screened by hybridization with the $^{32}$p-labeled mGluR8 probe prepared as described in Section II A. Before adding this DNA probe to the filters, the probe was denatured by heating at 100° C. for 10 minutes followed by chilling quickly on ice. The hybridization was carried out at 42° C. for 42 hours in a hybridization buffer containing: 50% Formamide; 5×SSPE (0.75 M NaCl, 50 mM $NaH_2PO_4.H_2O$, pH 7.4, 5 mM EDTA); 5× Denhardt's solution (1.0 g Ficoll, 1.0 g polyvinyl Pyrrolidone, 1.0 g BSA Pentax Fraction V, per liter of water); 0.1% SDS; and 100 µg/ml of denatured Salmon Sperm DNA. The buffer was carefully discarded and the filters were washed in wash buffer 1 (2×SSC containing 0.3 M NaCl, 0.03 M sodium citrate, pH 7.0, and 0.5% SDS) at room temperature for 1 hr followed by 2 washings in wash buffer 2 (1×SSC and 0.1% SDS) at 65° C. for 1 hr respectively. The filters were dried by blotting on Whatmam 3M Paper at room temperature and then autoradiographed using an intensifying screen to enhance this signal. After developing, the film was aligned with the filters to select positive plaques. 6 positive and 24 positive plaques were obtained when the library was screened with 5'-end probe (8P2+8P3, 332 bp) and 3'-end probes (8P8+8P9, 762 bp) respectively. Out of these positive plaques, three clones (#1, #7, #12) which matched with each other were picked and stored in 1 mL of SM buffer (0.1 M NaCl, 0.01 M $MgSO_4.7H_2O$, 0.035 M Tris-HCl (pH 7.5), 0.05% gelatin).

The plaques were diluted with SM buffer to obtain about 200–1000 plaques per filter (137 mm diameter) and then rescreened by hybridization with $^{32}$P-labeled mGluR8 probe as described above. A single well isolated positive plaque was isolated from each plate and stored in SM buffer. The cDNA inserts from these plaques were then excised in vivo and rescued into pBluescript® SK(-)plasmids according to the protocols recommended by the vendor (Stratagene, Inc., Lajolla, Calif., Catalog #200253). Ten to twelve white transformants were picked and grown in 3 mL of TY media containing 100 µg/mL of ampicillin. Plasmids were isolated from these cultures using the WIZARD™ Minipreps DNA purification System (Promega Corporation, Madison, Wis., Catalog #A7100) and analyzed for the presence of cDNA inserts after digestion with EcoRI and XhoI restriction enzymes by agarose (1%) gel electrophoresis. Those plasmids containing 3.17 kb inserts were selected for further amplification and purification. Nucleotide sequences were determined in both strands by using ABI DNA Sequencer (Applied Biosystems, Inc., Foster City, Calif.). The cDNA inserts in these plasmids contained coding region sequences of mGluR8 lacking the start codon ATG and 212 nucleotides following ATG at the 5'-end. One of these plasmids was designated as pBlue-mGluR8A.

C. Cloning the 5'-end of mGluR8 Gene

To obtain the missing nucleotides at the 5'-end, a primer pair containing a specific primer (SP2) based on the above partial coding sequences and a degenerate Primer (8P11) were designed for PCR amplification.

SP2: 5'-GCCTGCACGAATGTCAGAGACTGC-3' (SEQ ID NO:14)

8P11: 5'-GGYGGYCCCCCYWSYWSYGTNGC-3' (SEQ ID NO:15)

The first PCR reaction mixture (50 µl) contained: 10 µl of 5×PCR buffer, 8 µl of 2.5 mM dNTP mixture, 2 µl of Primer Mix containing 8P3 (SEQ ID NO:6) and 8P11 (SEQ ID NO:15) (20 pmoles each), 2.4 µl of TAQ DNA Polymerase-TaqStart™ antibody mixture (prepared as described previously), 5 µl of template (Clone #8 or #20 that was obtained from the first round screening with the 5'-Probe, but which did not match with the clones obtained with the 3'-Probe described above); and 22.6 µl of autoclaved distilled water. Amplification was done by touch down PCR using the following conditions: 1 minute denaturation at 95° C. (1 cycle); 30 second denaturation at 94° C.; 30 second annealing at 60° C.: 1 minute extension at 72° C. (20 cycles) with autodecrease of 0.5° C. per cycle followed by 30 second denaturation at 94° C.; 30 second annealing at 50° C. and 1 minute extension at 72° C. (10 Cycles). This incubation was continued at 72° C. for an additional 7 minutes and then the mixture was chilled at 4° C. A portion (1 µl) of this reaction mixture was used as a template for reamplification by second PCR using a primer pair of 8P11 (SEQ ID NO:15) and SP2 (Seq ID NO: 14). The conditions for PCR were as described previously. The resulting 425 bp fragment was purified by 1% gel electrophoresis and then subcloned into pCR-Script® SK(+)plasmid at the Srf-1 restriction site. About 12 white transformants were picked. Each was grown in 3 mL TY media containing 100 µg/mL ampicillin. Plasmids were isolated from these cultures using the Wizard Plus Minipreps DNA Purification System (Promega Corp., Madison, Wis., Catalog # A7100). DNA Sequence analysis of the insert confirmed the presence of human mGluR8 specific sequences corresponding to the 5'-end of the coding region and 5'-untranslated region. The plasmid containing partial 5'-end sequences of mGluR8 was designated as pCRScript.mGluR8.

D. Construction of Full Length cDNA Encoding mGluR8 Gene

A full length cDNA encoding mGluR8 gene was constructed by fusing partial coding sequences of mGluR8 gene in the plasmids pBlue.mGluR8A and pCRScript.mGluR8 as described below:

1) Isolation of bp AvaII/StuI restriction fragment from pBlue.mGluR8A

About 10 µg of plasmid pBlue.mGluR8A was suspended in 20 µl of 10×StuI buffer (500 mM Tris-HCl, pH 8.0, 100 mM $MgCl_2$, 500 mM NaCl), 20 µg of 1 mg/ml Bovine Serum Albumin (BSA), 2.5 µl (25 units) of StuI restriction enzyme (Gibco/BRL) and 160 µl of water. The components were gently mixed and incubated at 37_C for 2 hours. After checking a liquot of this mixture for complete digestion, the DNA was recovered using $QIA_{quick}$ Nucleotide Removal Kit (Quiagen Inc., Chatwsworth, Calif., Catalog # 28304). The resulting DNA digested with NotI by adding to the DNA, 10 µl of 10×NotI Buffer (500 mM Tris-HCl, pH 8.0, 100 mM $MgCl_2$, 1.0 M NaCL), 2.5 µl (25 units) of NotI Restriction enzyme (Gibco/BRL) and 37.5 µl of water (total volume of reaction is 100 µl). The solution was gently mixed and incubated at 37_C for 2 hours. The StuI-NotI fragments were purified by electrophoresis on a 1% low melting agarose gel. Both large and small StuI-NotI restriction fragments were sliced from the gel and the DNA was recovered by using $QIA_{quick}$ Gel Extraction Kit (Quiagen Inc., Chatsworth, Calif., Catalog # 28704). The DNA was stored in 50 µl of 10 mM Tris-HCl, pH 8.5. To 50 µl of the small StuI-NotI restriction fragment (580 bp) recovered above was added 20 µl of 10×AvaII buffer (500 mM potassium acetate, 200 mM Tris acetate, pH 7.9, 100 mM Magnesium acetate, 10 mM DTT), 20 µl of 1 mg/ml BSA, 110 µl of water and 2 µl (20 units) of Ava II restriction enzyme (New England BioLabs, Beverly, Mass.). The solution was gently mixed an incubated at 37_C for 2 hours. The DNA was precipitated with 20 µl of 3 M NaOAC and 1 ml of ethanol and then purified by electrophoresis on a 1.2% low melting agarose gel. The large AvaII-StuI restriction fragment (440 bp) was sliced from the gel and the DNA was recovered by using $QIA_{quick}$ Gel Extraction Kit (Quiagen, Inc., Chatsworth, Calif., Catalog # 28704). After precipitation and drying, the DNA was stored in 20 µl of 10 mM Tris-HCl, pH 8.0.

2) Isolation of 314 bp PCR fragment from pCRScript.m-GluR8

The PCR reaction mixture (100 μl) contained 10 μl of 10×PCR buffer (100 mM Tris-HCl, pH8.3, 500 mM KCl, 1.5 mM MgCl$_2$, and 0.01% gelatin, w/v), 1 μl of 2.5 mM dNTP mixture (dNTP=dATP+dTTP+dGTP+dCTP), 2 μl of Primer Mix containing 20 pmoles of:

SP-11

5'-GGGGCGGCCGCGTCGACTGCTGTGTTGCAAGA-3' SEQ ID NO:16 and 20 pmoles of:

SP2 5'-GCCTGCACGAATGTCAGAGACTGC-3' SEQ ID NO:14

1 μl of plasmid pCRScript.mGluR8 as a template, 0.5 μl (2.5 units) of Taq Polymerase (Gibco/BRL), and 40.5 μl of autoclaved distilled water. The contents of the tube were mixed and overlaid with 50 μl of mineral oil and then incubated in a DNA thermal cycler 480 (Perkin Elmer, Norwalk, Conn.). Amplification was performed using the following conditions: 1 min denaturing at 94_C; 1 minute annealing at 55_C; and 2 minutes extension at 72_C for a total of 30 cycles. The incubation was continued at 72_C for 7 minutes and the sample was then maintained at 4_C. The amplified PCR fragment was purified by using QIA$_{quick}$ PCR Purification Kit (Quiagen, Inc., Chattsworth, Calif., Catalog # 28104).

To 50 μl of purified PCR fragment was added 20 μl of 10×AvaII buffer, 20 μl of 1 mg/ml BSA, 110 μl of water and 3 μl (30 units) of AvaII restriction enzyme (New England BioLabs, Beverly, Mass., Catalog # 153). The solution was gently mixed and incubated at 37_C for 2 hours. The DNA was precipitated with 20 μl of 3 M NaOAC and 1 ml of ethanol. After keeping at −70_C for 2 hours, the DNA pellet was collected by centrifugation, washed once with 1 ml of 75% ethanol and then dried in vacuo for about 30 minutes. The pellet was redissolved in 20 μl of 10×NotI buffer, 20 μl of 1 mg/ml of BSA, 160 μl of water and 3 μl (30 units) of NotI restriction enzyme (Gibco/BRL). The solution was gently mixed and incubated at 37_C for 2 hours. The DNA was precipitated with 20 μl of 3 M NaOAC and 1 ml of ethanol and purified by electrophoresis on a 1% Low melting agarose gel. The NotI-AvaII restriction PCR fragment was sliced from the gel and the DNA was recovered by using QIA$_{quick}$ Gel Extraction Kit (Quiagen, Inc., Chatsworth, Calif., Catalog #28704). The DNA was stored in 50 μl of 10 mM Tris-Hcl (PH 8.5).

3) Construction of plasmid pBlue.mGluR8B

About 1.0 μl of vector pBlue.mGluR8A digested with restriction enzymes StuI and NotI (produced in section II D-1) was mixed with 1.5 μl of NotI/AvaII PCR fragment produced in section II D-1 and 5 μl of StuI/AvaII restriction fragment produced in section II D-1 in a tube contained 1 ul of 10×Prime Efficiency Ligation Buffer (5 Prime-3 Prime Inc., Boulder, Colo., Catalog #5301-576246), 1 μl of 50 mM DTT, 1–5 μl of water and 0.5 μl (2.0 units) T4 DNA Ligase. The reaction mixture was incubated at room temperature for 30 minutes and later at 65° C. for ten minutes. A portion of the mixture was transformed into E.Coli XL1-Blue competent cells according to protocols supplied by the vendor (Stratagene Inc., Lajolla, Calif.). The cells were plated on TY-agar plates supplemented with 100 μg/ml ampicillin and ten plates incubated at 37° C. overnight. About 12 ampicillin resistant colonies were picked from these plates and cultures grown at 37° C. overnight in 3 ml of TY media containing 100 μg/ml ampicillin plasmids were isolated from the cultures using WIZARD™ Minipreps DNA purification System(Promega Corp., Madison, Wis., Catalog #A7100). The desired plasmid designated pBlue.mGluR8B containing full length cDNA encoding mGluR8 gene was identified by the presence of 3.43 Kb SalI/KpnI restriction fragment as analyzed on 1% agarose gel.

III. Construction of Plasmid pGT-h.mGluR8

The CDNA insert encoding the mGluR8 gene in the plasmid pBlue.mGluR8B was subcloned into a pGT-h.MCS vector to form pGT-h.mGluR8 plasmid.

A. Isolation of SalI-KpnI Digested pGT-h vector

A 51 bp DNA fragment containing multiple cloning sites. (shown below (SEQ ID NO:17))

5'-TCGAGCCCGGGCTCTAGAGAGCTCGATATCGCG GCCGCGGTACCGTCGAGG-3'

3'-CGGGCCCGAGATCTCTCGAGCTATAGCGCCGGC GCCATGGCAGCTCC-5' was inserted into the SalI restriction Site in the expression vector pGT-h to form the expression vector pGT-h.MCS using standard techniques. About 10 μg of pGT-h.MCS plasmid was mixed with 20 μl of SalI buffer (1.5 M NaCl, 1.0 M Tris-HCl (pH 7.6), 100 μM MgCl$_2$, 20 μl of 1 mg/ml BSA 160 μl of water and 5 μl (50 units) of SalI restriction enzyme (Gibco/BRL, Gaithersburg, Md. Catalog # 15217-011). The mixture was incubated at 37° C. for 2 hours. The DNA was precipitated with 20 μl of 3 M NaOAC and 1 μl of Ethanol. After centrifugation and drying, the pellet was dissolved in 20 μl of 10×KpnI buffer (200 mM Tris-HCl pH 7.4, 50 mM MgCl$_2$, 500 mM KCl), 20 μl of 1 mg/ml BSA, 160 μl of water and 5 μl (50 units) of KpnI restriction enzyme (Gibco/BRL). After mixing, the reaction was incubated at 37° C. for 2 hours. The DNA was precipitated by adding 20 μl of 3 M NAOAC and 1 ml of ethanol, followed by mixing, chilling to −70° C. and centrifuging. The DNA was purified by electrophoresis on a 1% low melting agarose gel. The larger SalI-KpnI restriction fragment (7762 bp) was sliced from the gel and the DNA was recovered by QIA$_{quick}$ Gel Extraction Kit (Quiagen, Inc., Chaltsworth, Calif.): The DNA was stored in 50 μl of 10 mM Tris-HCl (pH 8.5)

B. Isolation of SalI-KpnI Restriction Fragment from pBlue.mGluR8B

About 15 μg of plasmid pBlue.mGluR8B was mixed with 20 μl of 10×ScaI buffer (500 mM NaCl, 500 mM KCl, 500 mM Tris-HCl, pH 7.4 and 60 mM MgCl$_2$), 20 μl of 1 mg/ml BSA, 160 μl of water and 5 μl (50 units) of ScaI restriction enzyme (Gibco/BRL, Gaithersburg, Md., Catalog # 15217-0011). After gentle mixing, the mixture was incubated at 37° C. for 2 hours. The DNA was precipitated with 20 μl of 3M NAOAC and 1 μl of ethanol. After centrifugation and drying, then pellet was dissolved in 160 μl of water and digested with SalI and KpnI restriction enzymes as described above (section II). After precipitation, centrifugation and drying, the DNA was purified by electrophoresis on 1.2% low melting agarose gel. The desired SalI-KpnI restriction fragment was sliced from the gel and the DNA was recovered by using QIA$_{quick}$ Gel Extraction Kit (Quiagen, Inc., Chatsworth, Calif., Catalog #28704). The DNA was stored in 50 μL of 10 mM Tris-HCl (pH 8.5).

C. Ligation and Transformation

About 0.5 μl of vector pGT-h.MCS digested with SalI and KpnI restriction enzymes was mixed with 5.5 μl of SalI-KpnI restriction fragment produced in section III B in a tube containing 1 μl of 10×Prime Efficiency Ligation Buffer (5 Prime-3 Prime Inc., Boulder, Colo., Catalog # 5301-576246), 1 μl of 50 mM DTT, 1.5 μl of water and 0.5 μl (2.0 units) of Ty DNA ligase. The reaction mixture was incubated at room temperature for 30 minutes and later at 65° C. for 10 minutes. A portion of the mixture was transformed into E.Coli XL-1 Blue Competent cells according to Protocols supplied by the vendor (Stratagene, Inc., Lajolla Calif.). The cells were plated on TY-agar plates supplemented with 100 μg/ml ampicillin and the plates incubated at 37° C. overnight.

About 24 ampicillin resistant colonies were picked and grown in 3 mL of TY media containing 100 μg/ml of ampicillin plasmids were isolated from these cultures using the WIZARD™ Minipreps DNA purification system (Promega Corporation, Madison, Wis. Catalog #A7100) and analyzed for the presence of cDNA inserts after digestion with SalI and KpnI restriction enzymes by agarose (1%) electrophoresis. Those plasmids containing 3.343 kb inserts were selected and analyzed further using PCR. One of these characterized plasmids was designated pGT-h.mGluR8. The cells harboring pGT-h.mGluR8 were grown and plasmid DNA was isolated from a 500 mL culture by the alkaline Lysis method and purified by Cesium Chloride-ethidium bromide gradient procedure as described in Molecular Cloning, A Laboratory Manual, Ed. Maniatis, T., Fritsche, E-F., and Sambrook, J., Cold Spring Harbor, N.Y. 90–94.

IV. Expression of Human mGluR8 in Mammalian Cells

Using standard techniques, the plasmid pGT-h.mGluR8 is transfected into the RGT cell line by the calcium phosphate precipitation method (see Graham et al, supra) and clones are selected for hygromycin resistance. Clones which express human mGluR8 are identified by measuring agonist (t-ACPD) mediated inhibition of forskolin stimulated adenyl cyclase using a commercially available cAMP assay kit.

V. Adenylate Cyclase Activity

Adenylate cyclase activity is determined in initial experiments in transfected mammalian cells, using standard techniques. See, e.g., N. Adham, et al., supra,; R. L. Weinshank, et al., *Proceedings of the National Academy of Sciences (USA)*, 89:3630–3634 (1992), and the references cited therein.

As noted above, mammalian cells (the cell line RGT is employed here) are stably transfected with the plasmid pGT-h.mGluR8, containing human mGluR8 cDNA inserted in the plasmid vector pGT-h. The cells are maintained in a medium consisting of Dulbecco's Modified Eagle's Medium (DMEM) containing 5% dialyzed fetal calf serum, 10 mM HEPES buffer (pH 7.3), 1 mM sodium pyruvate, 1 mM glutamine, and 200 µg/ml hygromycin.

For the assay the cells are disassociated from stock culture flasks with trypsin, and planted in 24-well plastic culture dishes (15 mm wells) at a density of 500–700,000 cells per well using the same culture medium. After twenty four hours incubation in a humidified carbon dioxide incubator, the cell monolayers are washed with buffer (Dulbecco's phosphate-buffered saline containing 0.5 mM isobutylmethylxanthine and 3 mM glucose) and then incubated in the same buffer at 37° C. for 30 minutes. The monolayers are then washed four additional times with buffer.

Drugs and forskolin, or forskolin alone, dissolved in buffer, are added after the final wash. After incubating for 20 minutes at 37° C., 0.5 ml of 8 mM EDTA is added to each well. The plates are then placed in a boiling water bath for about four minutes. The supernatant fluids are then recovered from the wells and lyophilized. Cyclic adenosinemonophosphate determinations are carried out on the lyophilized samples using commercially available radio immuno assay kits, following the manufacturer's instructions. The cAMP level in wells containing drug are the compared to the forskolin controls.

What is claimed is:

1. An isolated nucleic acid encoding a polypeptide functional as a human metabotropic glutamate receptor comprising the amino acid sequence given by SEQ ID NO:2 wherein said nucleic acid is selected from the group consisting of:
   (a) SEQ ID NO:1;
   (b) nucleotides 58 through 2781 of SEQ ID NO:1;
   (c) SEQ ID NO:3; and
   (d) nucleotides 58 through 2781 of SEQ ID NO:3.

2. A composition comprising an isolated nucleic acid as claimed in claim 1, wherein said sequence encoding a human glutamate receptor is selected from the group consisting of:
   (a) SEQ ID NO:1;
   (b) nucleotides 58 through 2781 of SEQ ID NO: 1;
   (c) SEQ ID NO:3; and
   (d) nucleotides 58 through 2781 of SEQ ID NO:3.

3. A composition as claimed in claim 2 wherein the isolated nucleic acid compound is deoxyribonucleic acid.

4. A composition as claimed in claim 3 wherein the isolated nucleic acid is set forth in (a).

5. A composition as claimed in claim 2 wherein the isolated nucleic acid compound is ribonucleic acid.

6. A composition as claimed in claim 5 wherein the isolated nucleic acid is set forth in (c).

7. A composition as claimed in claim 5 wherein the isolated nucleic acid is set forth in (d).

8. A composition as claimed in claim 3 wherein the isolated nucleic acid is set forth in (b).

9. A composition as claimed in claim 3 which is pGT-h.mGluR8.

10. An expression vector capable of encoding a human metabotropic glutamate receptor or a fragment thereof in a host cell which comprises a nucleic acid as claimed in claim 1 in combination with regulatory elements necessary for expression of the nucleic acid compound in the host cell.

11. An expression vector as claimed in claim 10 for use in a host cell wherein the host cell is a mammalian cell line.

12. An expression vector as claimed in claim 11 wherein the host cell is RGT-18.

13. A transfected host cell harboring an expression vector as claimed in claim 10.

14. A transfected host cell as claimed in claim 13 which is a transfected mammalian cell line.

15. A transfected host cell as claimed in claim 14 which is RGT-18 transfected with pGT-h.mGluR8.

16. A method of identifying a test compound as an agonist of a human mGluR8 which method comprises:
   a) introducing into a mammalian host cell an expression vector comprising DNA encoding a human mGluR8 receptor as given by SEQ ID NO:2, wherein said DNA is given by SEQ ID NO:1 or nucleotides 58 through 2781 of SEQ ID NO:1;
   b) culturing said host cell under conditions such that the human mGluR8 receptor is expressed;
   c) exposing said host cell expressing the human mGluR8 receptor to a test compound; and
   d) measuring the change in a physiological response known to be influenced by the binding of native ligand to the human mGluR8 receptor relative to a control in which the transfected host cell is exposed to native ligand.

17. A method of identifying a test compound as an antagonist of a human mGluR8 which method comprises:
   a) introducing into a mammalian host cell an expression vector comprising DNA encoding a human mGluR8 receptor as given by SEQ ID NO:2, wherein said DNA is given by SEQ ID NO:1 or nucleotides 58 through 2781 of SEO ID NO:1;
   b) culturing said host cell under conditions such that the human mGluR8 receptor is expressed;
   c) exposing said host cell expressing the human mGluR8 receptor to a test compound;
   d) exposing said host cell expressing the mGluR8 receptor to glutamate simultaneously with or following the exposure to the test compound; and
   e) measuring the change in a physiological response known to be influenced by the binding of glutamate to the human mGluR8 receptor relative to a control in which the transfected host cell is exposed to only glutamate.

18. A method of evaluating the effectiveness of a test compound for use as an agonist or antagonist of a human mGluR8 comprising the steps of:
   a) isolating a human mGluR8 receptor encoded by an isolated nucleic acid as claimed in claim 2;
   b) exposing said isolated human mGluR8 receptor to the test compound;
   c) exposing the isolated human mGluR8 receptor to glutamate simultaneously with or following the introduction of the test compound;
   d) removing non-specifically bound glutamate or test compound;
   e) quantifying the concentration of test compound or glutamate bound to the human mGluR8 receptor; and
   f) comparing the concentration of test compound or glutamate bound to the human mGluR8 receptor to a control in which no test compound was added.

* * * * *

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
        (A) LENGTH: 3321 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 58..2781

(xi) SEQUENCE DESCRIPTION: SEQ ID NO:1:

```
TGCTGTGTTG CAAGAATAAA CTTTGGGTCT TGGATTGCAA TACCACCTGT GGAGAAA          57

ATG GTA TGC GAG GGA AAG CGA TCA GCC TCT TGC CCT TGT TTC TTC CTC        105
Met Val Cys Glu Gly Lys Arg Ser Ala Ser Cys Pro Cys Phe Phe Leu
 1               5                  10                  15

TTG ACC GCC AAG TTC TAC TGG ATC CTC ACA ATG ATG CAA AGA ACT CAC        153
Leu Thr Ala Lys Phe Tyr Trp Ile Leu Thr Met Met Gln Arg Thr His
             20                  25                  30

AGC CAG GAG TAT GCC CAT TCC ATA CGG GTG GAT GGG GAC ATT ATT TTG        201
Ser Gln Glu Tyr Ala His Ser Ile Arg Val Asp Gly Asp Ile Ile Leu
         35                  40                  45

GGG GGT CTC TTC CCT GTC CAC GCA AAG GGA GAG AGA GGG GTG CCT TGT        249
Gly Gly Leu Phe Pro Val His Ala Lys Gly Glu Arg Gly Val Pro Cys
     50                  55                  60

GGG GAG CTG AAG AAG GAA AAG GGG ATT CAC AGA CTG GAG GCC ATG CTT        297
```

```
                    -continued

Gly Glu Leu Lys Lys Glu Lys Gly Ile His Arg Leu Glu Ala Met Leu
 65                  70                  75                  80

TAT GCA ATT GAC CAG ATT AAC AAG GAC CCT GAT CTC CTT TCC AAC ATC      345
Tyr Ala Ile Asp Gln Ile Asn Lys Asp Pro Asp Leu Leu Ser Asn Ile
                    85                  90                  95

ACT CTG GGT GTC CGC ATC CTC GAC ACG TGC TCT AGG GAC ACC TAT GCT      393
Thr Leu Gly Val Arg Ile Leu Asp Thr Cys Ser Arg Asp Thr Tyr Ala
                100                 105                 110

TTG GAG CAG TCT CTA ACA TTC GTG CAG GCA TTA ATA GAG AAA GAT GCT      441
Leu Glu Gln Ser Leu Thr Phe Val Gln Ala Leu Ile Glu Lys Asp Ala
                115                 120                 125

TCG GAT GTG AAG TGT GCT AAT GGA GAT CCA CCC ATT TTC ACC AAG CCC      489
Ser Asp Val Lys Cys Ala Asn Gly Asp Pro Pro Ile Phe Thr Lys Pro
            130                 135                 140

GAC AAG ATT TCT GGC GTC ATA GGT GCT GCA GCA AGC TCC GTG TCC ATC      537
Asp Lys Ile Ser Gly Val Ile Gly Ala Ala Ala Ser Ser Val Ser Ile
145                 150                 155                 160

ATG GTT GCT AAC ATT TTA AGA CTT TTT AAG ATA CCT CAA ATC AGC TAT      585
Met Val Ala Asn Ile Leu Arg Leu Phe Lys Ile Pro Gln Ile Ser Tyr
                    165                 170                 175

GCA TCC ACA GCC CCA GAG CTA AGT GAT AAC ACC AGG TAT GAC TTT TTC      633
Ala Ser Thr Ala Pro Glu Leu Ser Asp Asn Thr Arg Tyr Asp Phe Phe
                180                 185                 190

TCT CGA GTG GTT CCG CCT GAC TCC TAC CAA GCC CAA GCC ATG GTG GAC      681
Ser Arg Val Val Pro Pro Asp Ser Tyr Gln Ala Gln Ala Met Val Asp
                195                 200                 205

ATC GTG ACA GCA CTG GGA TGG AAT TAT GTT TCG ACA CTG GCT TCT GAG      729
Ile Val Thr Ala Leu Gly Trp Asn Tyr Val Ser Thr Leu Ala Ser Glu
            210                 215                 220

GGG AAC TAT GGT GAG AGC GGT GTG GAG GCC TTC ACC CAG ATC TCG AGG      777
Gly Asn Tyr Gly Glu Ser Gly Val Glu Ala Phe Thr Gln Ile Ser Arg
225                 230                 235                 240

GAG ATT GGT GGT GTT TGC ATT GCT CAG TCA CAG AAA ATC CCA CGT GAA      825
Glu Ile Gly Gly Val Cys Ile Ala Gln Ser Gln Lys Ile Pro Arg Glu
                    245                 250                 255

CCA AGA CCT GGA GAA TTT GAA AAA ATT ATC AAA CGC TGG CTA GAA ACA      873
Pro Arg Pro Gly Glu Phe Glu Lys Ile Ile Lys Arg Leu Leu Glu Thr
                260                 265                 270

CCT AAT GCT CGA GCA GTG ATT ATG TTT GCC AAT GAG GAT GAC ATC AGG      921
Pro Asn Ala Arg Ala Val Ile Met Phe Ala Asn Glu Asp Asp Ile Arg
                275                 280                 285

AGG ATA TTG GAA GCA GCA AAA AAA CTA AAC CAA AGT GGG CAT TTT CTC      969
Arg Ile Leu Glu Ala Ala Lys Lys Leu Asn Gln Ser Gly His Phe Leu
            290                 295                 300

TGG ATT GGC TCA GAT AGT TGG GGA TCC AAA ATA GCA CCT GTC TAT CAG     1017
Trp Ile Gly Ser Asp Ser Trp Gly Ser Lys Ile Ala Pro Val Tyr Gln
305                 310                 315                 320

CAA GAG GAG ATT GCA GAA GGG GCT GTG ACA ATT TTG CCC AAA CGA GCA     1065
Gln Glu Glu Ile Ala Glu Gly Ala Val Thr Ile Leu Pro Lys Arg Ala
                    325                 330                 335

TCA ATT GAT GGA TTT GAT CGA TAC TTT AGA AGC CGA ACT CTT GCC AAT     1113
Ser Ile Asp Gly Phe Asp Arg Tyr Phe Arg Ser Arg Thr Leu Ala Asn
                340                 345                 350

AAT CGA AGA AAT GTG TGG TTT GCA GAA TTC TGG GAG GAG AAT TTT GGC     1161
Asn Arg Arg Asn Val Trp Phe Ala Glu Phe Trp Glu Glu Asn Phe Gly
                355                 360                 365

TGC AAG TTA GGA TCA CAT GGG AAA AGG AAC AGT CAT ATA AAG AAA TGC     1209
Cys Lys Leu Gly Ser His Gly Lys Arg Asn Ser His Ile Lys Lys Cys
            370                 375                 380
```

```
ACA GGG CTG GAG CGA ATT GCT CGG GAT TCA TCT TAT GAA CAG GAA GGA      1257
Thr Gly Leu Glu Arg Ile Ala Arg Asp Ser Ser Tyr Glu Gln Glu Gly
385                 390                 395                 400

AAG GTC CAA TTT GTA ATT GAT GCT GTA TAT TCC ATG GCT TAC GCC CTG      1305
Lys Val Gln Phe Val Ile Asp Ala Val Tyr Ser Met Ala Tyr Ala Leu
                405                 410                 415

CAC AAT ATG CAC AAA GAT CTC TGC CCT GGA TAC ATT GGC CTT TGT CCA      1353
His Asn Met His Lys Asp Leu Cys Pro Gly Tyr Ile Gly Leu Cys Pro
            420                 425                 430

CGA ATG AGT ACC ATT GAT GGG AAA GAG CTA CTT GGT TAT ATT CGG GCT      1401
Arg Met Ser Thr Ile Asp Gly Lys Glu Leu Leu Gly Tyr Ile Arg Ala
        435                 440                 445

GTA AAT TTT AAT GGC AGT GCT GGC ACT CCT GTC ACT TTT AAT GAA AAC      1449
Val Asn Phe Asn Gly Ser Ala Gly Thr Pro Val Thr Phe Asn Glu Asn
    450                 455                 460

GGA GAT GCT CCT GGA CGT TAT GAT ATC TTC CAG TAT CAA ATA ACC AAC      1497
Gly Asp Ala Pro Gly Arg Tyr Asp Ile Phe Gln Tyr Gln Ile Thr Asn
465                 470                 475                 480

AAA AGC ACA GAG TAC AAA GTC ATC GGC CAC TGG ACC AAT CAG CTT CAT      1545
Lys Ser Thr Glu Tyr Lys Val Ile Gly His Trp Thr Asn Gln Leu His
                485                 490                 495

CTA AAA GTG GAA GAC ATG CAG TGG GCT CAT AGA GAA CAT ACT CAC CCG      1593
Leu Lys Val Glu Asp Met Gln Trp Ala His Arg Glu His Thr His Pro
            500                 505                 510

GCG TCT GTC TGC AGC CTG CCG TGT AAG CCA GGG GAG AGG AAG AAA ACG      1641
Ala Ser Val Cys Ser Leu Pro Cys Lys Pro Gly Glu Arg Lys Lys Thr
        515                 520                 525

GTG AAA GGG GTC CCT TGC TGC TGG CAC TGT GAA CGC TGT GAA GGT TAC      1689
Val Lys Gly Val Pro Cys Cys Trp His Cys Glu Arg Cys Glu Gly Tyr
    530                 535                 540

AAC TAC CAG GTG GAT GAG CTG TCC TGT GAA CTT TGC CCT CTG GAT CAG      1737
Asn Tyr Gln Val Asp Glu Leu Ser Cys Glu Leu Cys Pro Leu Asp Gln
545                 550                 555                 560

AGA CCC AAC ATG AAC CGC ACA GGC TGC CAG CTT ATC CCC ATC ATC AAA      1785
Arg Pro Asn Met Asn Arg Thr Gly Cys Gln Leu Ile Pro Ile Ile Lys
                565                 570                 575

TTG GAG TGG CAT TCT CCC TGG GCT GTG GTG CCT GTG TTT GTT GCA ATA      1833
Leu Glu Trp His Ser Pro Trp Ala Val Val Pro Val Phe Val Ala Ile
            580                 585                 590

TTG GGA ATC ATC GCC ACC ACC TTT GTG ATC GTG ACC TTT GTC CGC TAT      1881
Leu Gly Ile Ile Ala Thr Thr Phe Val Ile Val Thr Phe Val Arg Tyr
        595                 600                 605

AAT GAC ACA CCT ATC GTG AGG GCT TCA GGA CGC GAA CTT AGT TAC GTG      1929
Asn Asp Thr Pro Ile Val Arg Ala Ser Gly Arg Glu Leu Ser Tyr Val
    610                 615                 620

CTC CTA ACG GGG ATT TTT CTC TGT TAT TCA ATC ACG TTT TTA ATG ATT      1977
Leu Leu Thr Gly Ile Phe Leu Cys Tyr Ser Ile Thr Phe Leu Met Ile
625                 630                 635                 640

GCA GCA CCA GAT ACA ATC ATA TGC TCC TTC CGA CGG GTC TTC CTA GGA      2025
Ala Ala Pro Asp Thr Ile Ile Cys Ser Phe Arg Arg Val Phe Leu Gly
                645                 650                 655

CTT GGC ATG TGT TTC AGC TAT GCA GCC CTT CTG ACC AAA ACA AAC CGT      2073
Leu Gly Met Cys Phe Ser Tyr Ala Ala Leu Leu Thr Lys Thr Asn Arg
            660                 665                 670

ATC CAC CGA ATA TTT GAG CAG GGG AAG AAA TCT GTC ACA GCG CCC AAG      2121
Ile His Arg Ile Phe Glu Gln Gly Lys Lys Ser Val Thr Ala Pro Lys
        675                 680                 685

TTC ATT AGT CCA GCA TCT CAG CTG GTG ATC ACC TTC AGC CTC ATC TCC      2169
Phe Ile Ser Pro Ala Ser Gln Leu Val Ile Thr Phe Ser Leu Ile Ser
    690                 695                 700
```

```
GTC CAG CTC CTT GGA GTG TTT GTC TGG TTT GTT GTG GAT CCC CCC CAC      2217
Val Gln Leu Leu Gly Val Phe Val Trp Phe Val Val Asp Pro Pro His
705             710                 715                 720

ATC ATC ATT GAC TAT GGA GAG CAG CGG ACA CTA GAT CCA GAG AAG GCC      2265
Ile Ile Ile Asp Tyr Gly Glu Gln Arg Thr Leu Asp Pro Glu Lys Ala
                725                 730                 735

AGG GGA GTG CTC AAG TGT GAC ATT TCT GAT CTC TCA CTC ATT TGT TCA      2313
Arg Gly Val Leu Lys Cys Asp Ile Ser Asp Leu Ser Leu Ile Cys Ser
            740                 745                 750

CTT GGA TAC AGT ATC CTC TTG ATG GTC ACT TGT ACT GTT TAT GCC AAT      2361
Leu Gly Tyr Ser Ile Leu Leu Met Val Thr Cys Thr Val Tyr Ala Asn
        755                 760                 765

AAA ACG AGA GGT GTC CCA GAG ACT TTC AAT GAA GCC AAA CCT ATT GGA      2409
Lys Thr Arg Gly Val Pro Glu Thr Phe Asn Glu Ala Lys Pro Ile Gly
770             775                 780

TTT ACC ATG TAT ACC ACC TGC ATC ATT TGG TTA GCT TTC ATC CCC ATC      2457
Phe Thr Met Tyr Thr Thr Cys Ile Ile Trp Leu Ala Phe Ile Pro Ile
785             790                 795                 800

TTT TTT GGT ACA GCC CAG TCA GCA GAA AAG ATG TAC ATC CAG ACA ACA      2505
Phe Phe Gly Thr Ala Gln Ser Ala Glu Lys Met Tyr Ile Gln Thr Thr
                805                 810                 815

ACA CTT ACT GTC TCC ATG AGT TTA AGT GCT TCA GTA TCT CTG GGC ATG      2553
Thr Leu Thr Val Ser Met Ser Leu Ser Ala Ser Val Ser Leu Gly Met
            820                 825                 830

CTC TAT ATG CCC AAG GTT TAT ATT ATA ATT TTT CAT CCA GAA CAG AAT      2601
Leu Tyr Met Pro Lys Val Tyr Ile Ile Ile Phe His Pro Glu Gln Asn
        835                 840                 845

GTT CAA AAA CGC AAG AGG AGC TTC AAG GCT GTG GTG ACA GCT GCC ACC      2649
Val Gln Lys Arg Lys Arg Ser Phe Lys Ala Val Val Thr Ala Ala Thr
850             855                 860

ATG CAA AGC AAA CTG ATC CAA AAA GGA AAT GAC AGA CCA AAT GGC GAG      2697
Met Gln Ser Lys Leu Ile Gln Lys Gly Asn Asp Arg Pro Asn Gly Glu
865             870                 875                 880

GTG AAA AGT GAA CTC TGT GAG AGT CTT GAA ACC AAC ACT TCC TCT ACC      2745
Val Lys Ser Glu Leu Cys Glu Ser Leu Glu Thr Asn Thr Ser Ser Thr
                885                 890                 895

AAG ACA ACA TAT ATC AGT TAC AGC AAT CAT TCA ATC TGAAACAGGG           2791
Lys Thr Thr Tyr Ile Ser Tyr Ser Asn His Ser Ile
                900                 905

AAATGGCACA ATCTGAAGAG ACGTGGTATA TGATCTTAAA TGATGAACAT GAGACCGCAA    2851

AAATTCACTC CTGGAGATCT CCGTAGACTA CAATCAATCA AATCAATAGT CAGTCTTGTA    2911

AGGAACAAAA ATTAGCCATG AGCCAAAAGT ATCAATAAAC GGGGAGTGAA GAAACCCGTT    2971

TTATACAATA AAACCAATGA GTGTCAAGCT AAAGTATTGC TTATTCATGA GCAGTTAAAA    3031

CAAATCACAA AAGGAAAACT AATGTTAGCT CGTGAAAAAA ATGCTGTTGA AATAAATAAT    3091

GTCTGATGTT ATTCTTGTAT TTTTCTGTGA TTGTGAGAAC TCCCGTTCCT GTCCCACATT    3151

GTTTAACTTG TATAAGACAA TGAGTCTGTT TCTTGTAATG GCTGACCAGA TTGAAGCCCT    3211

GGGTTGTGCT AAAAATAAAT GCAATGATTG ATGCATGCAA TTTTTTATAC AAATAATTTA    3271

TTTCTAATAA TAAAGGAATG TTTTGCAAAA AAAAAAAAAA AAAACTCGAG               3321

(2) INFORMATION FOR SEQ ID NO:2:

(i) SEQUENCE CHARACTERISTICS:
          (A) LENGTH: 908 amino acids
          (B) TYPE: amino acid
          (D) TOPOLOGY: linear
```

-continued (ii) MOLECULE TYPE: protein (xi) SEQUENCE DESCRIPTION: SEQ ID NO:2:

```
Met Val Cys Glu Gly Lys Arg Ser Ala Ser Cys Pro Cys Phe Phe Leu
  1               5                  10                  15

Leu Thr Ala Lys Phe Tyr Trp Ile Leu Thr Met Met Gln Arg Thr His
             20                  25                  30

Ser Gln Glu Tyr Ala His Ser Ile Arg Val Asp Gly Asp Ile Ile Leu
         35                  40                  45

Gly Gly Leu Phe Pro Val His Ala Lys Gly Glu Arg Gly Val Pro Cys
 50                  55                  60

Gly Glu Leu Lys Lys Glu Lys Gly Ile His Arg Leu Glu Ala Met Leu
 65                  70                  75                  80

Tyr Ala Ile Asp Gln Ile Asn Lys Asp Pro Asp Leu Leu Ser Asn Ile
                 85                  90                  95

Thr Leu Gly Val Arg Ile Leu Asp Thr Cys Ser Arg Asp Thr Tyr Ala
             100                 105                 110

Leu Glu Gln Ser Leu Thr Phe Val Gln Ala Leu Ile Glu Lys Asp Ala
         115                 120                 125

Ser Asp Val Lys Cys Ala Asn Gly Asp Pro Pro Ile Phe Thr Lys Pro
130                 135                 140

Asp Lys Ile Ser Gly Val Ile Gly Ala Ala Ser Ser Val Ser Ile
145                 150                 155                 160

Met Val Ala Asn Ile Leu Arg Leu Phe Lys Ile Pro Gln Ile Ser Tyr
                 165                 170                 175

Ala Ser Thr Ala Pro Glu Leu Ser Asp Asn Thr Arg Tyr Asp Phe Phe
             180                 185                 190

Ser Arg Val Val Pro Pro Asp Ser Tyr Gln Ala Gln Ala Met Val Asp
         195                 200                 205

Ile Val Thr Ala Leu Gly Trp Asn Tyr Val Ser Thr Leu Ala Ser Glu
210                 215                 220

Gly Asn Tyr Gly Glu Ser Gly Val Glu Ala Phe Thr Gln Ile Ser Arg
225                 230                 235                 240

Glu Ile Gly Gly Val Cys Ile Ala Gln Ser Gln Lys Ile Pro Arg Glu
                 245                 250                 255

Pro Arg Pro Gly Glu Phe Glu Lys Ile Ile Lys Arg Leu Leu Glu Thr
             260                 265                 270

Pro Asn Ala Arg Ala Val Ile Met Phe Ala Asn Glu Asp Asp Ile Arg
         275                 280                 285

Arg Ile Leu Glu Ala Ala Lys Lys Leu Asn Gln Ser Gly His Phe Leu
290                 295                 300

Trp Ile Gly Ser Asp Ser Trp Gly Ser Lys Ile Ala Pro Val Tyr Gln
305                 310                 315                 320

Gln Glu Glu Ile Ala Glu Gly Ala Val Thr Ile Leu Pro Lys Arg Ala
                 325                 330                 335

Ser Ile Asp Gly Phe Asp Arg Tyr Phe Arg Ser Arg Thr Leu Ala Asn
             340                 345                 350

Asn Arg Arg Asn Val Trp Phe Ala Glu Phe Trp Glu Glu Asn Phe Gly
         355                 360                 365

Cys Lys Leu Gly Ser His Gly Lys Arg Asn Ser His Ile Lys Lys Cys
370                 375                 380

Thr Gly Leu Glu Arg Ile Ala Arg Asp Ser Ser Tyr Glu Gln Glu Gly
385                 390                 395                 400
```

```
Lys Val Gln Phe Val Ile Asp Ala Val Tyr Ser Met Ala Tyr Ala Leu
                405                 410                 415

His Asn Met His Lys Asp Leu Cys Pro Gly Tyr Ile Gly Leu Cys Pro
            420                 425                 430

Arg Met Ser Thr Ile Asp Gly Lys Glu Leu Leu Gly Tyr Ile Arg Ala
        435                 440                 445

Val Asn Phe Asn Gly Ser Ala Gly Thr Pro Val Thr Phe Asn Glu Asn
    450                 455                 460

Gly Asp Ala Pro Gly Arg Tyr Asp Ile Phe Gln Tyr Gln Ile Thr Asn
465                 470                 475                 480

Lys Ser Thr Glu Tyr Lys Val Ile Gly His Trp Thr Asn Gln Leu His
                485                 490                 495

Leu Lys Val Glu Asp Met Gln Trp Ala His Arg Glu His Thr His Pro
            500                 505                 510

Ala Ser Val Cys Ser Leu Pro Cys Lys Pro Gly Glu Arg Lys Lys Thr
        515                 520                 525

Val Lys Gly Val Pro Cys Cys Trp His Cys Glu Arg Cys Glu Gly Tyr
    530                 535                 540

Asn Tyr Gln Val Asp Glu Leu Ser Cys Glu Leu Cys Pro Leu Asp Gln
545                 550                 555                 560

Arg Pro Asn Met Asn Arg Thr Gly Cys Gln Leu Ile Pro Ile Ile Lys
                565                 570                 575

Leu Glu Trp His Ser Pro Trp Ala Val Val Pro Val Phe Val Ala Ile
            580                 585                 590

Leu Gly Ile Ile Ala Thr Thr Phe Val Ile Val Thr Phe Val Arg Tyr
        595                 600                 605

Asn Asp Thr Pro Ile Val Arg Ala Ser Gly Arg Glu Leu Ser Tyr Val
    610                 615                 620

Leu Leu Thr Gly Ile Phe Leu Cys Tyr Ser Ile Thr Phe Leu Met Ile
625                 630                 635                 640

Ala Ala Pro Asp Thr Ile Ile Cys Ser Phe Arg Arg Val Phe Leu Gly
                645                 650                 655

Leu Gly Met Cys Phe Ser Tyr Ala Ala Leu Leu Thr Lys Thr Asn Arg
            660                 665                 670

Ile His Arg Ile Phe Glu Gln Gly Lys Lys Ser Val Thr Ala Pro Lys
        675                 680                 685

Phe Ile Ser Pro Ala Ser Gln Leu Val Ile Thr Phe Ser Leu Ile Ser
    690                 695                 700

Val Gln Leu Leu Gly Val Phe Val Trp Phe Val Val Asp Pro Pro His
705                 710                 715                 720

Ile Ile Ile Asp Tyr Gly Glu Gln Arg Thr Leu Asp Pro Glu Lys Ala
                725                 730                 735

Arg Gly Val Leu Lys Cys Asp Ile Ser Asp Leu Ser Leu Ile Cys Ser
            740                 745                 750

Leu Gly Tyr Ser Ile Leu Leu Met Val Thr Cys Thr Val Tyr Ala Asn
        755                 760                 765

Lys Thr Arg Gly Val Pro Glu Thr Phe Asn Glu Ala Lys Pro Ile Gly
    770                 775                 780

Phe Thr Met Tyr Thr Thr Cys Ile Ile Trp Leu Ala Phe Ile Pro Ile
785                 790                 795                 800

Phe Phe Gly Thr Ala Gln Ser Ala Glu Lys Met Tyr Ile Gln Thr Thr
                805                 810                 815

Thr Leu Thr Val Ser Met Ser Leu Ser Ala Ser Val Ser Leu Gly Met
```

```
                820              825              830
Leu Tyr Met Pro Lys Val Tyr Ile Ile Ile Phe His Pro Glu Gln Asn
            835              840              845
Val Gln Lys Arg Lys Arg Ser Phe Lys Ala Val Thr Ala Ala Thr
    850              855              860
Met Gln Ser Lys Leu Ile Gln Lys Gly Asn Asp Arg Pro Asn Gly Glu
865              870              875              880
Val Lys Ser Glu Leu Cys Glu Ser Leu Glu Thr Asn Thr Ser Thr
                885              890              895
Lys Thr Thr Tyr Ile Ser Tyr Ser Asn His Ser Ile
            900              905
```

(2) INFORMATION FOR SEQ ID NO:3:

(i) SEQUENCE CHARACTERISTICS:
        (A) LENGTH: 3321 base pairs
        (B) TYPE: nucleic acid
        (C) STRANDEDNESS: single
        (D) TOPOLOGY: linear (ii) MOLECULE TYPE: mRNA (xi) SEQUENCE DESCRIPTION: SEQ ID NO:3:

```
UGCUGUGUUG CAAGAAUAAA CUUUGGGUCU UGGAUUGCAA UACCACCUGU GGAGAAAAUG    60
GUAUGCGAGG GAAAGCGAUC AGCCUCUUGC CCUUGUUUCU UCCUCUUGAC CGCCAAGUUC   120
UACUGGAUCC UCACAAUGAU GCAAAGAACU CACAGCCAGG AGUAUGCCCA UUCCAUACGG   180
GUGGAUGGGG ACAUUAUUUU GGGGGGUCUC UUCCCUGUCC ACGCAAAGGG AGAGAGAGGG   240
GUGCCUUGUG GGGAGCUGAA GAAGGAAAAG GGGAUUCACA GACUGGAGGC CAUGCUUUAU   300
GCAAUUGACC AGAUUAACAA GGACCCUGAU CUCCUUUCCA ACAUCACUCU GGGUGUCCGC   360
AUCCUCGACA CGUGCUCUAG GGACACCUAU GCUUUGGAGC AGUCUCUAAC AUUCGUGCAG   420
GCAUUAAUAG AGAAAGAUGC UUCGGAUGUG AAGUGUGCUA AUGGAGAUCC ACCCAUUUUC   480
ACCAAGCCCG ACAAGAUUUC UGGCGUCAUA GGUGCUGCAG CAAGCUCCGU GUCCAUCAUG   540
GUUGCUAACA UUUUAAGACU UUUUAAGAUA CCUCAAAUCA GCUAUGCAUC CACAGCCCCA   600
GAGCUAAGUG AUAACACCAG GUAUGACUUU UUCUCUCGAG UGGUUCCGCC UGACUCCUAC   660
CAAGCCCAAG CCAUGGUGGA CAUCGUGACA GCACUGGGAU GGAAUUAUGU UUCGACACUG   720
GCUUCUGAGG GGAACUAUGG UGAGAGCGGU GUGGAGGCCU UCACCCAGAU CUCGAGGGAG   780
AUUGGUGGUG UUUGCAUUGC UCAGUCACAG AAAAUCCCAC GUGAACCAAG ACCUGGAGAA   840
UUUGAAAAAA UUAUCAAACG CCUGCUAGAA ACACCUAAUG CUCGAGCAGU GAUUAUGUUU   900
GCCAAUGAGG AUGACAUCAG GAGGAUAUUG GAAGCAGCAA AAAACUAAA CCAAAGUGGG   960
CAUUUUCUCU GGAUUGGCUC AGAUAGUUGG GGAUCCAAAA UAGCACCUGU CUAUCAGCAA  1020
GAGGAGAUUG CAGAAGGGGC UGUGACAAUU UGCCCAAAC GAGCAUCAAU UGAUGGAUUU  1080
GAUCGAUACU UUAAGAGCCG AACUCUUGCC AAUAAUCGAA GAAAUGUGUG UUUGCAGAA  1140
UUCUGGGAGG AGAAUUUUGG CUGCAAGUUA GGAUCACAUG GGAAAAGGAA CAGUCAUAUA  1200
AAGAAAUGCA CAGGGCUGGA GCGAAUUGCU CGGGAUUCAU CUUAUGAACA GGAAGGAAAG  1260
GUCCAAUUUG UAAUUGAUGC UGUAUAUUCC AUGGCUUACG CCCUGCACAA UAUGCACAAA  1320
GAUCUCUGCC CUGGAUACAU UGGCCUUUGU CCACGAAUGA GUACCAUUGA UGGGAAAGAG  1380
CUACUUGGUU AUAUUCGGGC UGUAAAUUUU AAUGGCAGUU CUGGCACUCC UGUCACUUUU  1440
AAUGAAAACG GAGAUGCUCC UGGACGUUAU GAUAUCUUCC AGUAUCAAAU AACCAACAAA  1500
```

```
AGCACAGAGU ACAAAGUCAU CGGCCACUGG ACCAAUCAGC UUCAUCUAAA AGUGGAAGAC    1560

AUGCAGUGGG CUCAUAGAGA ACAUACUCAC CCGGCGUCUG UCUGCAGCCU GCCGUGUAAG    1620

CCAGGGGAGA GGAAGAAAAC GGUGAAAGGG GUCCCUUGCU GCUGGCACUG UGAACGCUGU    1680

GAAGGUUACA ACUACCAGGU GGAUGAGCUG UCCUGUGAAC UUUGCCCUCU GGAUCAGAGA    1740

CCCAACAUGA ACCGCACAGG CUGCCAGCUU AUCCCCAUCA UCAAAUUGGA GUGGCAUUCU    1800

CCCUGGGCUG UGGUGCCUGU GUUUGUUGCA AUAUUGGGAA UCAUCGCCAC CACCUUUGUG    1860

AUCGUGACCU UUGUCCGCUA UAAUGACACA CCUAUCGUGA GGGCUUCAGG ACGCGAACUU    1920

AGUUACGUGC UCCUAACGGG GAUUUUCUC UGUUAUUCAA UCACGUUUUU AAUGAUUGCA    1980

GCACCAGAUA CAAUCAUAUG CUCCUUCCGA CGGGUCUUCC UAGGACUUGG CAUGUGUUUC    2040

AGCUAUGCAG CCCUUCUGAC CAAAACAAAC CGUAUCCACC GAAUAUUUGA GCAGGGGAAG    2100

AAAUCUGUCA CAGCGCCCAA GUUCAUUAGU CCAGCAUCUC AGCUGGUGAU CACCUUCAGC    2160

CUCAUCUCCG UCCAGCUCCU UGGAGUGUUU GUCUGGUUUG UUGUGGAUCC CCCCCACAUC    2220

AUCAUUGACU AUGGAGAGCA GCGGACACUA GAUCCAGAGA AGGCCAGGGG AGUGCUCAAG    2280

UGUGACAUUU CUGAUCUCUC ACUCAUUUGU UCACUGGAU ACAGUAUCCU CUUGAUGGUC    2340

ACUUGUACUG UUUAUGCCAA UAAAACGAGA GGUGUCCCAG AGACUUUCAA UGAAGCCAAA    2400

CCUAUUGGAU UUACCAUGUA UACCACCUGC AUCAUUUGGU UAGCUUUCAU CCCCAUCUUU    2460

UUUGGUACAG CCCAGUCAGC AGAAAAGAUG UACAUCCAGA CAACAACACU UACUGUCUCC    2520

AUGAGUUUAA GUGCUUCAGU AUCUCUGGGC AUGCUCUAUA UGCCCAAGGU UUAUAUUAUA    2580

AUUUUUCAUC CAGAACAGAA UGUUCAAAAA CGCAAGAGGA GCUUCAAGGC UGUGGUGACA    2640

GCUGCCACCA UGCAAAGCAA ACUGAUCCAA AAAGGAAAUG ACAGACCAAA UGGCGAGGUG    2700

AAAAGUGAAC UCUGUGAGAG UCUUGAAACC AACACUUCCU CUACCAAGAC AACAUAUAUC    2760

AGUUACAGCA AUCAUUCAAU CUGAAACAGG GAAAUGGCAC AAUCUGAAGA GACGUGGUAU    2820

AUGAUCUUAA AUGAUGAACA UGAGACCGCA AAAAUUCACU CCUGGAGAUC UCCGUAGACU    2880

ACAAUCAAUC AAAUCAAUAG UCAGUCUUGU AAGGAACAAA AAUUAGCCAU GAGCCAAAAG    2940

UAUCAAUAAA CGGGGAGUGA AGAAACCCGU UUUAUACAAU AAAACCAAUG AGUGUCAAGC    3000

UAAAGUAUUG CUUAUUCAUG AGCAGUUAAA ACAAAUCACA AAAGGAAAAC UAAUGUUAGC    3060

UCGUGAAAAA AAUGCUGUUG AAAUAAAUAA UGUCUGAUGU UAUUCUUGUA UUUUUCUGUG    3120

AUUGUGAGAA CUCCCGUUCC UGUCCCACAU UGUUUAACUU GUAUAAGACA AUGAGUCUGU    3180

UUCUUGUAAU GGCUGACCAG AUUGAAGCCC UGGGUUGUGC UAAAAAUAAA UGCAAUGAUU    3240

GAUGCAUGCA AUUUUUUAUA CAAAUAAUUU AUUUCUAAUA AUAAAGGAAU GUUUUGCAAA    3300

AAAAAAAAAA AAAAACUCGA G                                              3321
```

(2) INFORMATION FOR SEQ ID NO:4:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:4:

TGSGAGGGMA AGMGSWSMAC CWSNTGYCC                                                    29

(2) INFORMATION FOR SEQ ID NO:5:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:5:

ATGATGCARA GRACYCACAG CCARGA                                                       26

(2) INFORMATION FOR SEQ ID NO:6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:6:

GTCKCCRTTR GCRACCTTCA CRTC                                                         24

(2) INFORMATION FOR SEQ ID NO:7:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:7:

KGCRGCRCCK ATSACRCCRS WRATYTTRTC                                                    30

(2) INFORMATION FOR SEQ ID NO:8:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:8:

WSMGGMWSMCAYGGSAAGAMGNCGNAA                                                        27

(2) INFORMATION FOR SEQ ID NO:9:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:9:

GTCYTCCACY TTYAGGTGMA GYTGRTT                          27

(2) INFORMATION FOR SEQ ID NO:10:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:10:

SACRSWYGCK GGGTGSGTGT GCTCYCKRTT                      30

(2) INFORMATION FOR SEQ ID NO:11:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:11:

GCMCCYGACA CMATCATCTG YWSYTT                          26

(2) INFORMATION FOR SEQ ID NO:12:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:12:

RSWRSWRGTG TTGGTYTCMA GRCT                            24

(2) INFORMATION FOR SEQ ID NO:13:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:13:

RTGRTCRCTG TAGCTGATGT AKGTKGT                                            27

(2) INFORMATION FOR SEQ ID NO:14:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:14:

GCCTGCACGA ATGTCAGAGA CTGC                                               24

(2) INFORMATION FOR SEQ ID NO:15:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:15:

GGYGGYCCCC CYWSYWSYGT NGC                                                23

(2) INFORMATION FOR SEQ ID NO:16:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:16:

GGGGCGGCCG CGTCGACTGC TGTGTTGCAA GA                                      32

(2) INFORMATION FOR SEQ ID NO:17:

(i) SEQUENCE CHARACTERISTICS:
        (A) LENGTH: 51 base pairs
        (B) TYPE: nucleic acid

```
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:17:

TCGAGCCCGG GCTCTAGAGA GCTCGATATC GCGGCCGCGG TACCGTCGAG G                51
```